US012714343B2

(12) United States Patent
Oida et al.

(10) Patent No.: US 12,714,343 B2
(45) Date of Patent: Aug. 25, 2026

(54) BRAIN MEASUREMENT APPARATUS

(71) Applicants: HAMAMATSU PHOTONICS K.K., Hamamatsu (JP); Kyoto University, Kyoto (JP)

(72) Inventors: Takenori Oida, Hamamatsu (JP); Takahiro Moriya, Hamamatsu (JP); Akinori Saito, Hamamatsu (JP); Motohiro Suyama, Hamamatsu (JP); Yosuke Ito, Kyoto (JP); Hiroyuki Ueda, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 172 days.

(21) Appl. No.: 18/809,624

(22) Filed: Aug. 20, 2024

(65) Prior Publication Data

US 2025/0072804 A1 Mar. 6, 2025

(30) Foreign Application Priority Data

Sep. 5, 2023 (JP) ................................ 2023-143519

(51) Int. Cl.
*G01V 3/00* (2006.01)
*A61B 5/00* (2006.01)
(Continued)

(52) U.S. Cl.
CPC ............ *A61B 5/245* (2021.01); *A61B 5/0042* (2013.01); *A61B 5/055* (2013.01)

(58) Field of Classification Search
CPC ........ A61B 5/245; A61B 5/0042; A61B 5/055
(Continued)

(56) References Cited

U.S. PATENT DOCUMENTS 10,782,368 B2 9/2020 Bulatowicz et al.
2022/0091200 A1 3/2022 Gerginov

FOREIGN PATENT DOCUMENTS

JP 2020146286 A * 9/2020 ............. A61B 5/372

OTHER PUBLICATIONS

Limes, M.E. et al., "Portable Magnetometry for Detection of Biomagnetism in Ambient Environments," Physical Review Applied 14, 011002, Jun. 2, 2020.

(Continued)

*Primary Examiner* — Walter L Lindsay, Jr.
*Assistant Examiner* — Frederick Wenderoth
(74) *Attorney, Agent, or Firm* — Faegre Drinker Biddle & Reath LLP

(57) ABSTRACT

A brain measurement apparatus includes: a magnetoencephalograph module having a cell; a pump laser configured to emit pump light; a probe laser configured to emit probe light; an optical sensor group configured to detect a polarization plane angle of the probe light having passed through the sensitivity region; a bias magnetic field coil configured to apply a bias magnetic field; and bias magnetic field gradient correction coils configured to correct a gradient of the bias magnetic field; and an MRI module having a transmission coil for transmitting an RF pulse of a predetermined frequency and a receiver coil configured to detect a nuclear magnetic resonance signal. At least one of the coil that applies a static magnetic field and the coil that applies a gradient magnetic field is configured by the same coil as the bias magnetic field coil or the bias magnetic field gradient correction coils.

7 Claims, 13 Drawing Sheets

(51) Int. Cl.
*A61B 5/055* (2006.01)
*A61B 5/245* (2021.01)

(58) Field of Classification Search
USPC .......................................................... 324/304
See application file for complete search history.

(56) References Cited

OTHER PUBLICATIONS

Lucivero, V.G. et al., "Femtotesla Nearly-Quantum-Noise-Limited Pulsed Gradiometer at Earth-Scale Fields," Phys. Rev. Applied 18, L021001, Dec. 17, 2021.

* cited by examiner

GRADIENT CORRECTION POWER SUPPLY
108
M1
11
121
122
104
14
12,13
1A
y
z
x
122
1
124
114
14
11
12,13
105
109
CONTROL DEVICE
SWITCH
MRI POWER SUPPLY
106
BIAS MAGNETIC FIELD POWER SUPPLY
107

1
4
21
22
23a
23b
23c
6
25
26a
26b
26c
26d
27a
27b
27c
27d
2
3
Bz
Bm
Rf
5
7
31a
31b
31c
32a
32b
32c
33
34a
34b
34c
34d
41a
42a
43a
43b
43c
43d
8
9
10
x
y
z 45a 45b 45c 45d
43a 43b 43c 43d
44a 44b 44c 44d
42a 42b 42c 42d
41a 41b 41c 41d
ARa ARb ARc ARd
Rf
Bm
2
QLa QLb QLc QLd
34a 34b 34c 34d
7
5
31a 32a 31b 32b 31c 32c 33

1A
Bm
5
35
7
34d
34c
33
32c
31c
32b
31b
32a
31a
37
QLd
2
QLc
3
PL
34b
34a
QLb
QLa
4
21
22
6
43d
43c
43b
27a
23a
9
43a
Bz
Rf
x
y
z

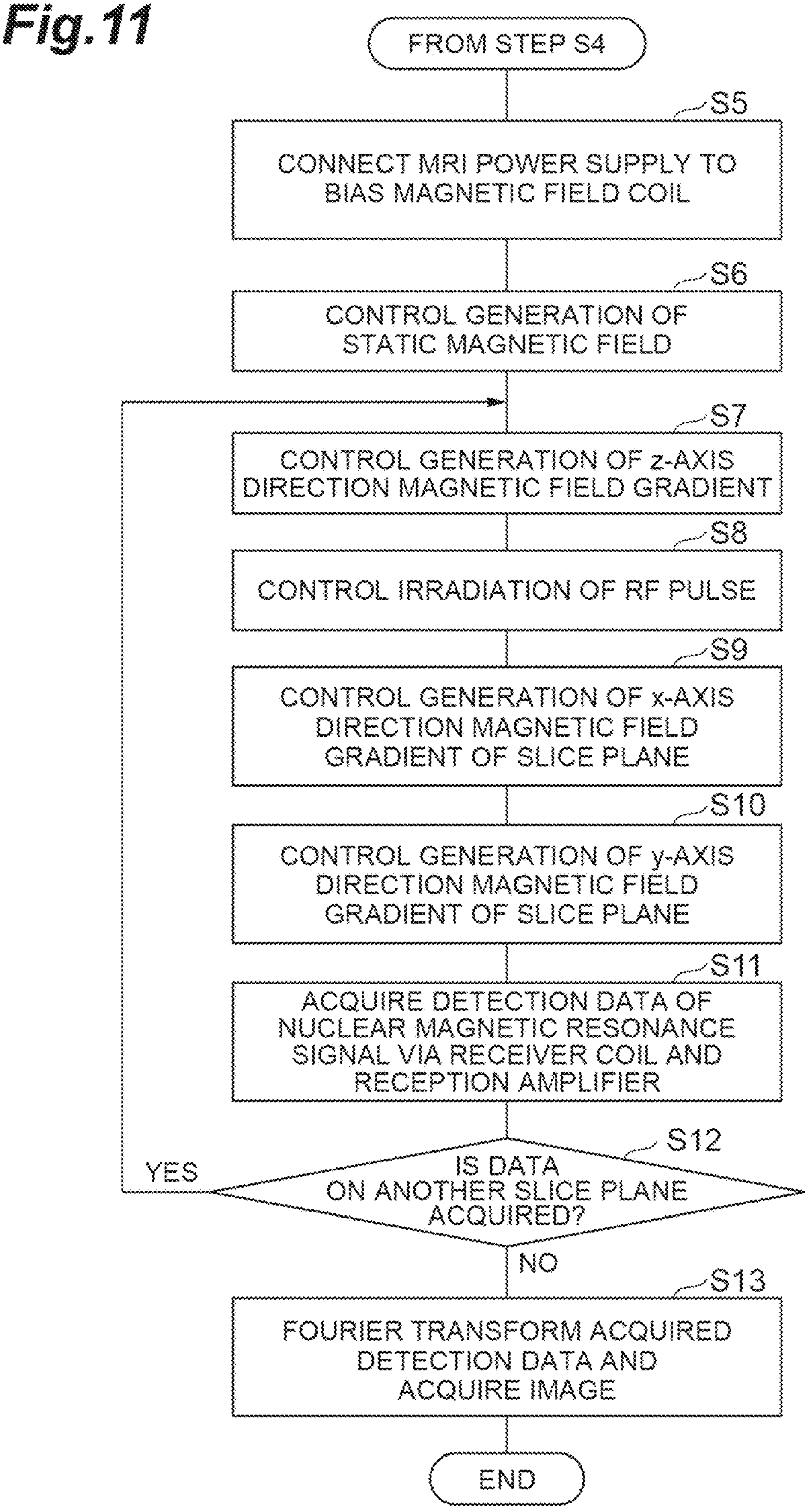

Fig.11
FROM STEP S4
S5
CONNECT MRI POWER SUPPLY TO BIAS MAGNETIC FIELD COIL
S6
CONTROL GENERATION OF STATIC MAGNETIC FIELD
S7
CONTROL GENERATION OF z-AXIS DIRECTION MAGNETIC FIELD GRADIENT
S8
CONTROL IRRADIATION OF RF PULSE
S9
CONTROL GENERATION OF x-AXIS DIRECTION MAGNETIC FIELD GRADIENT OF SLICE PLANE
S10
CONTROL GENERATION OF y-AXIS DIRECTION MAGNETIC FIELD GRADIENT OF SLICE PLANE
S11
ACQUIRE DETECTION DATA OF NUCLEAR MAGNETIC RESONANCE SIGNAL VIA RECEIVER COIL AND RECEPTION AMPLIFIER
S12
IS DATA ON ANOTHER SLICE PLANE ACQUIRED?
YES
NO
S13
FOURIER TRANSFORM ACQUIRED DETECTION DATA AND ACQUIRE IMAGE
END

BRAIN MEASUREMENT APPARATUS

TECHNICAL FIELD

One aspect of the embodiment relates to a brain measurement apparatus.

BACKGROUND

A photoexcitation magnetic sensor capable of measuring a weak external magnetic field is known (see, for example, US Patent Publication No. 2022/0091200 and U.S. Pat. No. 10,782,368). In the photoexcitation magnetic sensor, alkali metal atoms in a cell are excited by pump light, probe light irradiated toward the cell so as to intersect the pump light is measured by an optical sensor, and an intensity of the external magnetic field is detected based on an output of the optical sensor.

SUMMARY

The inventors of the present application have studied an apparatus capable of measuring a brain magnetic field and acquiring a brain morphological image by fusing a conventional photoexcitation magnetic sensor as described above and a magnetic resonance imaging (MRI) apparatus. In order to realize the apparatus in which the photoexcitation magnetic sensor and the MRI apparatus are fused, it is desired to downsize the apparatus.

Therefore, one aspect of the embodiment has been made in view of such a problem, and an object thereof is to provide a brain measurement apparatus that realizes measurement of a brain magnetic field and acquisition of a brain morphological image by a miniaturized configuration.

A brain measurement apparatus according to a first aspect of the embodiment includes: a magnetoencephalograph having: a cell in which alkali metal vapor is filled, a pump laser configured to emit pump light for exciting alkali metal atoms constituting the alkali metal vapor, a probe laser configured to emit probe light for detecting a change in electron spin in an excited state of the alkali metal atoms to a sensitivity region intersecting the pump light in the cell, an optical sensor configured to detect a polarization plane angle of the probe light having passed through the sensitivity region, a bias magnetic field coil configured to apply a bias magnetic field in a same direction as the pump light and determine a resonance frequency of the electron spin, and a bias magnetic field gradient correction coil configured to correct a gradient of the bias magnetic field; and an MRI apparatus having: a static magnetic field coil for applying a static magnetic field, a gradient magnetic field coil for applying a gradient magnetic field, a transmission coil for transmitting a transmission pulse of a predetermined frequency, and a receiver coil configured to detect a nuclear magnetic resonance signal generated by transmission of the transmission pulse, in which at least one of the static magnetic field coil and the gradient magnetic field coil is configured by a same coil as the bias magnetic field coil or the bias magnetic field gradient correction coil.

According to the first aspect, the pump light is emitted in a state where a bias magnetic field with a corrected gradient is applied to a cell filled with an alkali metal, whereby the electron spin of the alkali metal atoms are generated (excited). Further, the probe light is emitted to the sensitivity region intersecting the pump light in the cell, the polarization plane angle of the probe light having passed through the sensitivity region is detected by the optical sensor, and an intensity of the brain magnetic field in the sensitivity region can be measured based on the detected polarization plane angle. In addition, according to the first aspect, the static magnetic field and the gradient magnetic field are applied by the static magnetic field coil and the gradient magnetic field coil, and the nuclear magnetic resonance signal generated by transmission of the transmission pulse is detected by the receiver coil, whereby a brain morphological image (MR image) can be measured. Here, in the brain measurement apparatus according to the first aspect, at least one of the static magnetic field coil and the gradient magnetic field coil, which are components of the MRI apparatus, is commonly used as the bias magnetic field coil or the bias magnetic field gradient correction coil, which are components of the magnetoencephalograph. As a result, the measurement of the brain magnetic field and the acquisition of the brain morphological image (MR image) can be realized by a miniaturized configuration.

In the first aspect, it is preferable that the static magnetic field coil is configured by the same coil as the bias magnetic field coil. In this case, the bias magnetic field and the static magnetic field can be stably applied by the commonly used coil, and stable measurement can be realized.

Further, in the first aspect, it is also preferable that the gradient magnetic field coil is configured by the same coil as the bias magnetic field gradient correction coil. As a result, correction of the gradient of the bias magnetic field and application of the gradient magnetic field can be stably performed by the commonly used coil, and stable measurement can be realized.

Furthermore, in the first aspect, it is also preferable that the magnetoencephalograph further has tilting device for tilting a direction of the electron spin in a direction perpendicular to the pump light. In this case, by measuring the intensity of the brain magnetic field based on the frequency of the change in the polarization plane angle of the detected probe light, the measurement sensitivity of the brain magnetic field can be maintained without being affected by an environmental magnetic field.

In addition, in the first aspect, it is preferable that the magnetoencephalograph has two or more sensitivity regions where the pump light and the probe light intersect with each other, and measures the brain magnetic field based on a difference between outputs of the optical sensors corresponding to two adjacent sensitivity regions. In this case, by using the difference between the outputs of the optical sensors corresponding to the two adjacent sensitivity regions, common mode noise common to the two sensitivity regions is removed, and the measurement of the weak brain magnetic field can be realized.

Furthermore, in the first aspect, it is also preferable that the tilting devices irradiates an RF pulse having a same frequency as the resonance frequency. In this case, the measurement of the brain magnetic field based on the frequency of the change in the polarization plane angle of the probe light can be realized by simple means.

Furthermore, in the first aspect, it is also preferable that the tilting devices irradiates pulsed light. In this way, the measurement of the brain magnetic field based on the frequency of the change in the polarization plane angle of the probe light can be realized by simple means.

A brain measurement apparatus according to the embodiment is [1] "a brain measurement apparatus including a magnetoencephalograph having:

a cell in which alkali metal vapor is filled, a pump laser configured to emit pump light for exciting alkali metal atoms constituting the alkali metal vapor, a probe laser configured to emit probe light for detecting a change in electron spin in an excited state of the alkali metal atoms to a sensitivity region intersecting the pump light in the cell, an optical sensor configured to detect a polarization plane angle of the probe light having passed through the sensitivity region, a bias magnetic field coil configured to apply a bias magnetic field in a same direction as the pump light and determine a resonance frequency of the electron spin, and a bias magnetic field gradient correction coil configured to correct a gradient of the bias magnetic field; and an MRI apparatus having:

a static magnetic field coil for applying a static magnetic field, a gradient magnetic field coil for applying a gradient magnetic field, a transmission coil for transmitting a transmission pulse of a predetermined frequency, and a receiver coil configured to detect a nuclear magnetic resonance signal generated by transmission of the transmission pulse, in which at least one of the static magnetic field coil and the gradient magnetic field coil is configured by a same coil as the bias magnetic field coil or the bias magnetic field gradient correction coil".

The brain measurement apparatus according to the embodiment may be [2] "the brain measurement apparatus described in [1] above, in which the static magnetic field coil is configured by a same coil as the bias magnetic field coil".

The brain measurement apparatus according to the embodiment may be [3] "the brain measurement apparatus described in [1] or [2] above, in which the gradient magnetic field coil is configured by a same coil as the bias magnetic field gradient correction coil".

The brain measurement apparatus according to the embodiment may be [4] "the brain measurement apparatus described in any of [1] to [3] above, in which the magnetoencephalograph further has tilting devices for tilting a direction of the electron spin in a direction perpendicular to the pump light".

The brain measurement apparatus according to the embodiment may be [5] "the brain measurement apparatus described in any of [1] to [4] above, in which the magnetoencephalograph has two or more sensitivity regions where the pump light and the probe light intersect with each other, and measures a brain magnetic field based on a difference between outputs of the optical sensors corresponding to two adjacent sensitivity regions".

The brain measurement apparatus according to the embodiment may be [6] "the brain measurement apparatus described in [4] above, in which the tilting devices irradiates an RF pulse having a same frequency as the resonance frequency".

The brain measurement apparatus according to the embodiment may be [7] "the brain measurement apparatus described in [4] above, in which the tilting devices irradiates pulsed light".

BRIEF DESCRIPTION OF THE DRAWINGS

FIG. 11 is a flowchart illustrating the operation of the brain measurement apparatus according to the embodiment;

DETAILED DESCRIPTION

Figure 1:
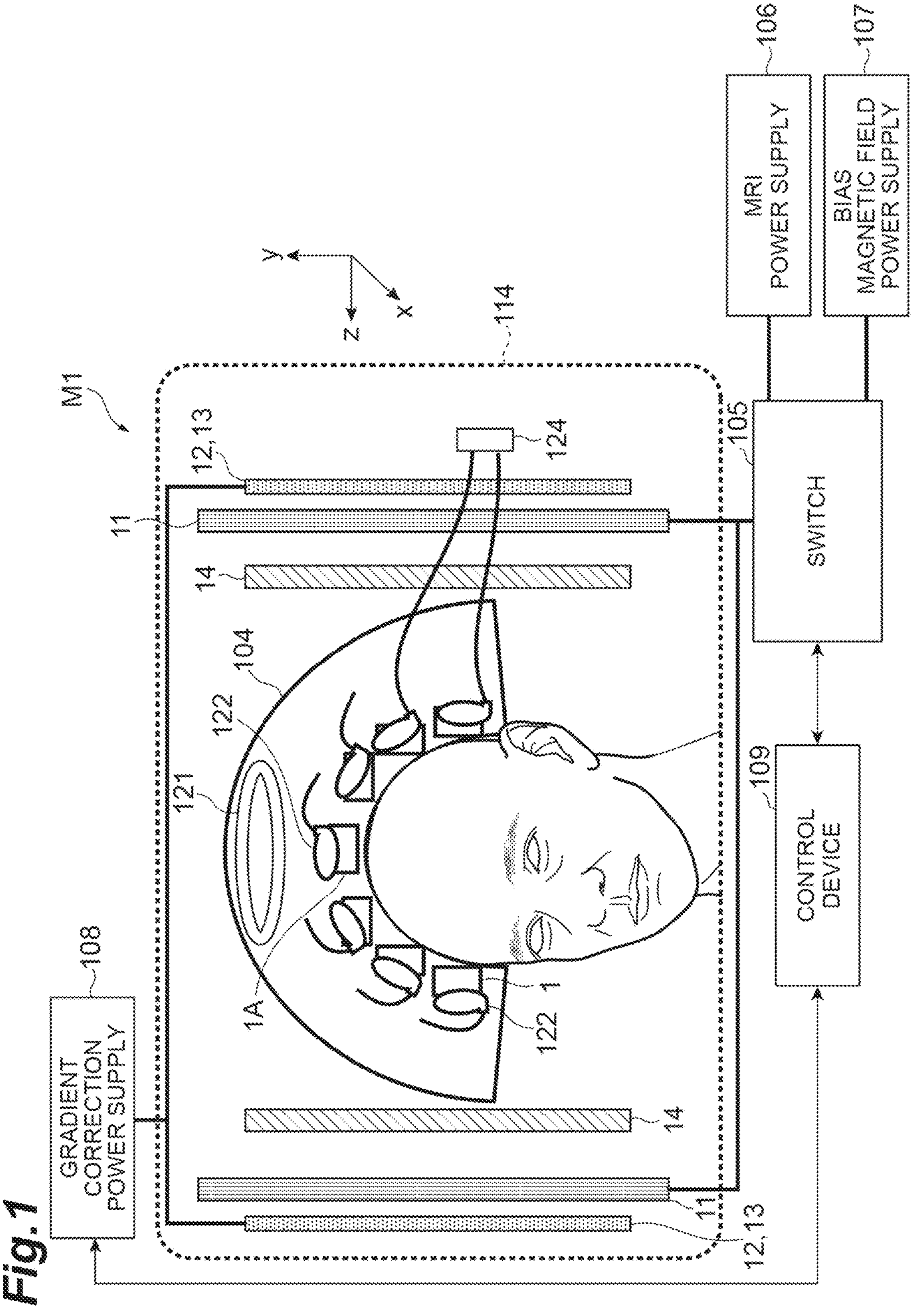
FIG. 1 is a schematic view illustrating a configuration of a brain measurement apparatus according to an embodiment.

Hereinafter, an embodiment of the present invention will be described in detail with reference to the accompanying drawings. In the description, the same reference numeral is used for the same component or a component having the same function, and redundant description is omitted.

FIG. 1 is a schematic view illustrating a configuration of a brain measurement apparatus M1 according to an embodiment. The brain measurement apparatus M1 is an apparatus that measures a brain magnetic field and measures a magnetic resonance (MR) image, which is a brain morphological image, for a subject. The brain measurement apparatus M1 includes a magnetoencephalograph module having two types of photoexcitation magnetic sensors (optically pumped magnetometers) 1 and 1A, a nonmagnetic frame 104, a bias magnetic field coil 11, bias magnetic field gradient correction coils 12 and 13, and a tilting coil 14, an MRI module having a transmission coil 121, a plurality of receiver coils 122, and a reception amplifier 124, and an electromagnetic shield 114. Furthermore, the brain measurement apparatus M1 includes a power supply device including a switch 105, an MRI power supply 106, a bias magnetic field power supply 107, and a gradient correction power supply 108, and a control device 109 that controls the power supply device and the like.

In the following description, a direction approximately parallel to a central axis of a head of the subject is defined as a y-axis direction, and directions perpendicular to the y-axis and perpendicular to each other are defined as a z-axis direction and an x-axis direction. In the following description, a positive direction and a negative direction along the x-axis are referred to as a +x-axis direction and a −x-axis direction, respectively, a positive direction and a negative direction along the y-axis are referred to as a +y-axis direction and a −y-axis direction, respectively, and a positive direction and a negative direction along the z-axis are referred to as a +z-axis direction and a −z-axis direction, respectively.

The nonmagnetic frame 104 is a frame covering the entire region of a scalp of the subject to be measured for the brain magnetic field, and is made of a nonmagnetic material such as graphite having a relative permeability close to 1 and not disturbing magnetic field distribution. The nonmagnetic frame 104 can be, for example, a helmet-type frame that surrounds the entire scalp of the subject and is attached on the head of the subject. A plurality of photoexcitation magnetic sensors 1 and 1A are fixed to the nonmagnetic frame 104 so as to be close to the scalp of the subject. Furthermore, the receiver coils 122 for detecting a nuclear magnetic resonance signal for MR image measurement are fixed on the opposite side of the plurality of photoexcitation magnetic sensors 1 and 1A to the scalp of the subject in the nonmagnetic frame 104. The receiver coil 122 detects a nuclear magnetic resonance signal of a proton to be described later and converts it into a current.

The plurality of photoexcitation magnetic sensors 1A are disposed at predetermined intervals around the y-axis so as to surround the head near the top of the head of the subject, for example. The plurality of photoexcitation magnetic sensors 1 are disposed at predetermined intervals around the y-axis so as to surround the head away from the photoexcitation magnetic sensors 1A in the −y-axis direction.

Figure 2:
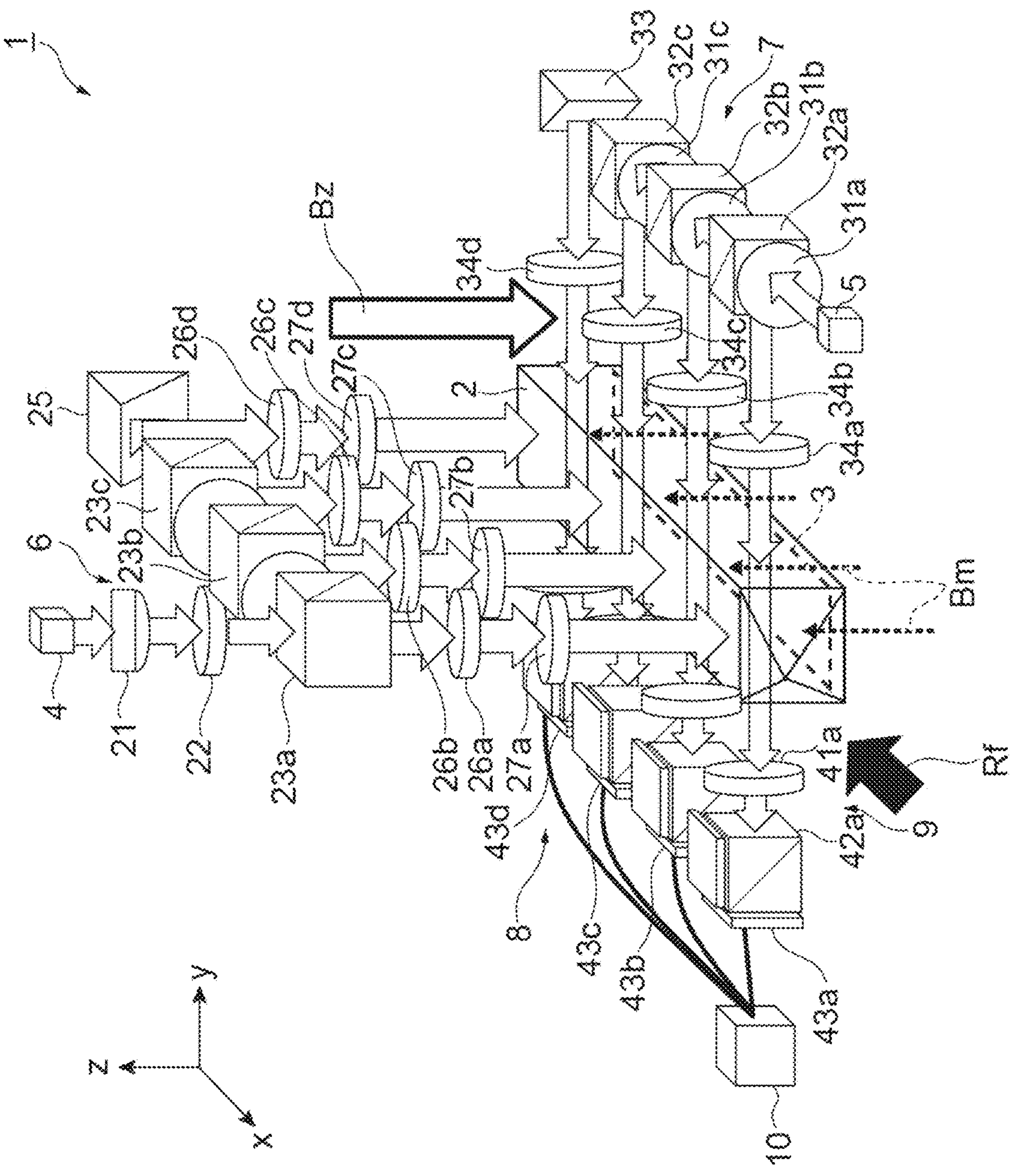
FIG. 2 is a perspective view illustrating a configuration of a photoexcitation magnetic sensor of FIG. 1.

FIG. 2 is a perspective view illustrating a configuration of the photoexcitation magnetic sensor 1 according to the embodiment. The photoexcitation magnetic sensor 1 is a device that measures a brain magnetic field using optical pumping. The photoexcitation magnetic sensor 1 has a configuration capable of measuring a brain magnetic field along the z-axis direction. As described later, the direction along the y-axis corresponds to an incident direction of the probe light in the measurement region, and the direction along the z-axis corresponds to an incident direction of the pump light in the measurement region.

As illustrated in FIG. 2, the photoexcitation magnetic sensor 1 includes a cell 2, a heater 3, a pump laser 4, a probe laser 5, a first optical system 6, a second optical system 7, an optical sensor group 8, a third optical system 9, and a readout circuit 10. Note that the pump laser 4, the probe laser 5, and the readout circuit 10 may be shared with another photoexcitation magnetic sensor 1 or with the plurality of photoexcitation magnetic sensors 1A. Hereinafter, the components of the photoexcitation magnetic sensor 1 will be described in detail.

The cell 2 is a container that is filled with alkali metal vapor. The cell 2 is disposed along the direction along the x-axis. The cell 2 has a substantially rectangular parallelepiped shape having a plane substantially parallel to an xy plane and a bottomed cylindrical shape. The cross section of the cell 2 in a direction perpendicular to a longitudinal direction of the cell 2 (direction along a yz plane) is, for example, a square. The cell 2 may be made of a material such as quartz, sapphire, silicon, Kovar glass, or borosilicate glass, for example. The cell 2 has optical transparency with respect to pump light and probe light to be described later. The heater 3 and the like are attached to a side surface of the cell 2 in the −z-axis direction. A magnetic field Bm to be measured generated from a measurement target is incident on the side surface of the cell 2 in the −z-axis direction along the +z-axis direction.

The alkali metal constituting the alkali metal vapor filled in the cell 2 may be, for example, at least one or more type of lithium (Li), sodium (Na), potassium (K), rubidium (Rb), and cesium (Cs). For example, the alkali metal may be potassium and rubidium, or may be only potassium. Potassium has a relatively low spin-destruction collision relaxation rate among alkali metals used in photoexcitation magnetic sensors. The spin-destruction collision relaxation rate of potassium is smaller than, for example, cesium and rubidium. Therefore, when a single alkali metal is adopted, the photoexcitation magnetic sensor using only potassium has higher sensitivity than the photoexcitation magnetic sensor using only cesium or only rubidium.

In addition, the cell 2 contains filling gas. The filling gas suppresses relaxation of the spin polarization of the alkali metal vapor. The filling gas also protects alkali metal vapor and suppresses noise emission. The filling gas may be, for example, an inert gas such as helium (He), neon (Ne), argon (Ar), krypton (Kr), xenon (Xe), or nitrogen (N2). The filling gas may be, for example, helium and nitrogen.

As described above, the heater 3 is attached to the cell 2. The heater 3 generates heat according to a current supplied from a heater power supply (not illustrated). The heater 3 controls a vapor density of the alkali metal by controlling an internal temperature of the cell 2. For example, when potassium is contained as the alkali metal in the cell 2, the heater 3 heats the cell 2 so that the internal temperature of the cell 2 becomes 100° C.

The pump laser 4 emits pump light for exciting alkali metal atoms in the −z-axis direction. That is, the pump laser 4 emits linearly polarized pump light. The alkali metal atoms contained in the cell 2 are excited by pump light in a circularly polarized state, and spin polarization is generated. A wavelength of the pump light is set according to the type of atoms constituting the alkali metal vapor (more specifically, a wavelength of an absorption line). For example, when the atom constituting the alkali metal vapor is potassium, the wavelength of the pump light is set to 770.11 nm according to a resonance line of potassium. When the alkali metal atoms contained in the cell 2 are potassium and rubidium, the pump laser 4 may emit pump light for exciting the atoms of rubidium and transferring the spin polarization of the atom of rubidium to the atom of potassium. In this case, the atom of rubidium is excited by the pump light. Then, due to a spin exchange interaction between potassium and rubidium, the spin polarization of the atom of rubidium is transferred to the atom of potassium, and the atom of potassium is in an excited state.

Figure 3:
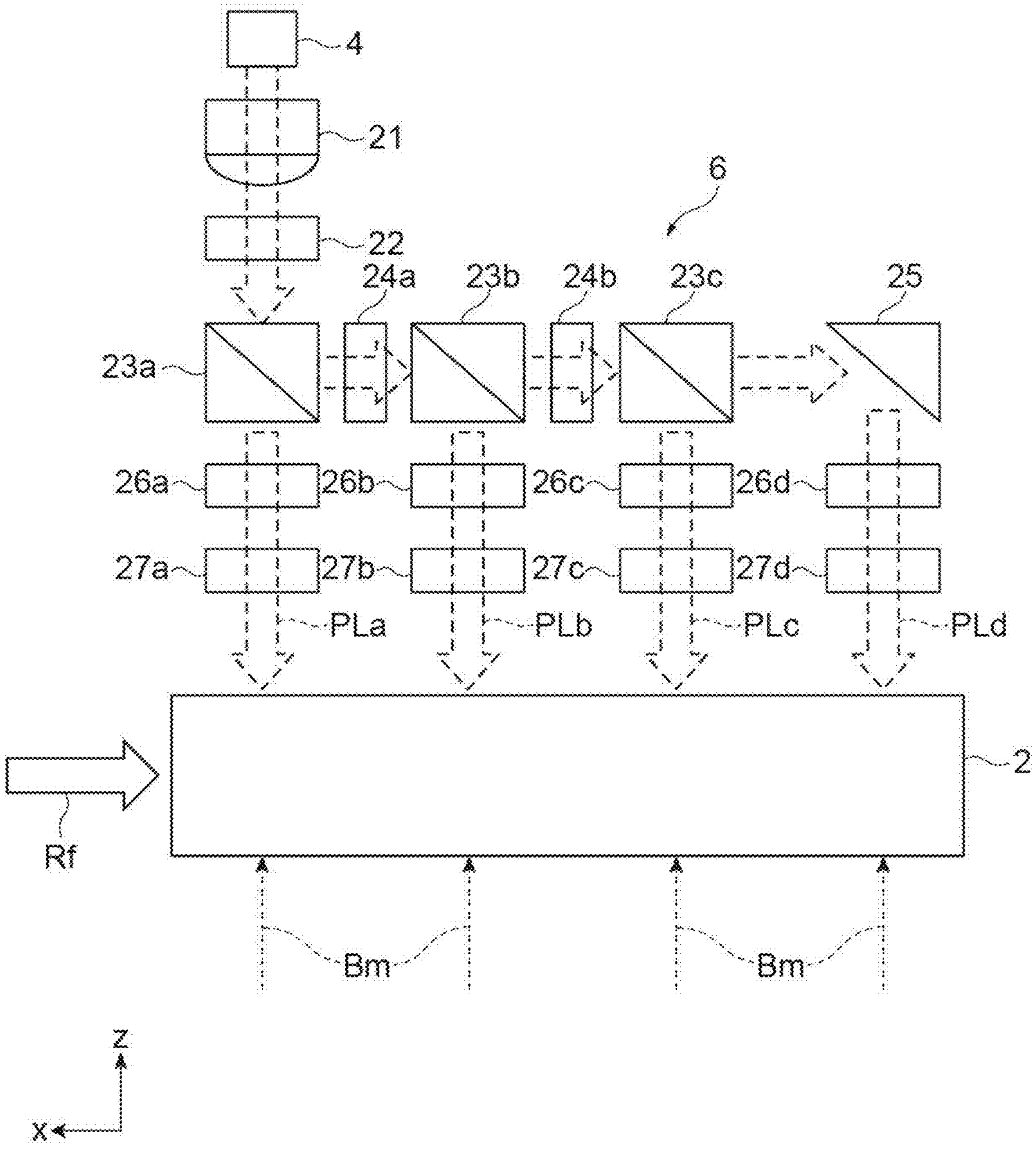
FIG. 3 is a plan view of a first optical system in FIG. 2 as viewed in a −y-axis direction.

The pump light from the pump laser 4 enters the cell 2 via the first optical system 6. FIG. 3 is a plan view of the first optical system 6 as viewed in the −y-axis direction. The first optical system 6 includes a lens 21, a ½ wavelength plate 22, polarization beam splitters 23*a*, 23*b*, and 23*c*, ½ wavelength plates 24*a* and 24*b*, a total reflection mirror 25, polarizers 26*a*, 26*b*, 26*c*, and 26*d*, and ¼ wavelength plates 27*a*, 27*b*, 27*c*, and 27*d*.

The lens 21 is provided adjacent to the pump laser 4 in the −z-axis direction, and condenses the pump light emitted from the pump laser 4. The ½ wavelength plate 22 is provided adjacent to the lens 21 in the −z-axis direction, and rotates a polarization plane such that the power of the pump laser is distributed 1:3 by the polarization beam splitter 23*a*.

The polarization beam splitter 23*a* is provided adjacent to the ½ wavelength plate 22 in the −z-axis direction, separates two linearly polarized light components perpendicular to each other from the polarized light component of the pump light transmitted through the ½ wavelength plate 22, transmits one linearly polarized light component in the −z-axis direction, and reflects the other linearly polarized light component in the −x-axis direction. The polarization beam splitters 23*b* and 23*c* and the total reflection mirror 25 are provided side by side in order in the −x-axis direction with respect to the polarization beam splitter 23*a*. The polarization beam splitters 23*b* and 23*c* separate two linearly polarized light components perpendicular to each other from the pump light transmitted through the polarization beam splitters 23*a* and 23*b*, respectively, transmit one linearly polarized light component in the −x-axis direction, and reflect the other linearly polarized light component in the −z-axis direction. The total reflection mirror 25 reflects the linearly polarized pump light transmitted through the polarization beam splitter 23*c* in the −z-axis direction.

The ½ wavelength plate 24*a* is provided between the polarization beam splitter 23*a* and the polarization beam splitter 23*b*, and rotates the polarization plane of the linearly polarized pump light reflected by the polarization beam splitter 23*a*. Thus, the pump light can be separated into two linearly polarized light components by the polarization beam splitter 23*b*. The ½ wavelength plate 24*b* is provided between the polarization beam splitter 23*b* and the polarization beam splitter 23*c*, and rotates the polarization plane of the linearly polarized pump light transmitted through the polarization beam splitter 23*b*. Thus, the pump light can be separated into two linearly polarized light components by the polarization beam splitter 23*c*.

The polarizer 26*a* and the ¼ wavelength plate 27*a* are provided adjacent to the polarization beam splitter 23*a* in order in the −z-axis direction. The polarizer 26*a* transmits a specific linearly polarized light component of the pump light transmitted through the polarization beam splitter 23*a*, and the ¼ wavelength plate 27*a* changes the polarization state of the pump light transmitted through the polarizer 26*a* to circularly polarized light and transmits the circularly polarized light as pump light PLa in the −z-axis direction.

The polarizers 26*b*, 26*c*, and 26*d* and the ¼ wavelength plates 27*b*, 27*c*, and 27*d* are provided adjacent to the polarization beam splitters 23*b* and 23*c* and the total reflection mirror 25 in order in the −z-axis direction, respectively. The functions of the polarizers 26*b*, 26*c*, and 26*d* and the ¼ wavelength plates 27*b*, 27*c*, and 27*d* are the same as those of the polarizer 26*a* and the ¼ wavelength plate 27*a*, respectively, and transmit pump lights PLb, PLc, and PLd in the −z-axis direction.

The first optical system 6 having the above configuration is configured such that four systems of pump lights PLa to PLd transmitting through the four ¼ wavelength plates 27*a*, 27*b*, 27*c*, and 27*d* can be incident on regions separated in a longitudinal direction (direction along the x-axis) in the cell 2.

The probe laser 5 emits, in the −y-axis direction, probe light for detecting precession motion of spin when the electron spin in the excited state of the alkali metal atom is tilted by 90 degrees. That is, the probe laser 5 emits linearly polarized probe light. When the probe light passes through the alkali metal vapor, a magneto-optical rotation angle changes under the influence of the state of spin polarization of the alkali metal atom. By detecting the change in the magneto-optical rotation angle, the state of the precession motion of the spin can be derived. The wavelength of the probe light is set according to the type of atoms constituting the alkali metal vapor (more specifically, the wavelength of the absorption line). For example, when only potassium is contained as the alkali metal in the cell 2, the wavelength of the probe light is detuned from the wavelength of the pump light (for example, 770.11 nm), and is set to, for example, about 770.05 nm. Since the wavelength of the probe light is detuned from the wavelength of the pump light, absorption of the probe light by potassium is suppressed.

When potassium and rubidium are contained in the cell 2 as the alkali metals, the probe laser 5 may emit probe light for detecting the change in the magneto-optical rotation angle caused by the spin polarization in the excited state of the atom of potassium. A density of rubidium used for excitation is set to be smaller than a density of potassium used for the probe. When the density of rubidium is smaller than the density of potassium, attenuation of pump light due to excitation is suppressed. Thus, the photoexcitation magnetic sensor 1 can obtain uniform sensitivity in the cell 2.

Figure 4:
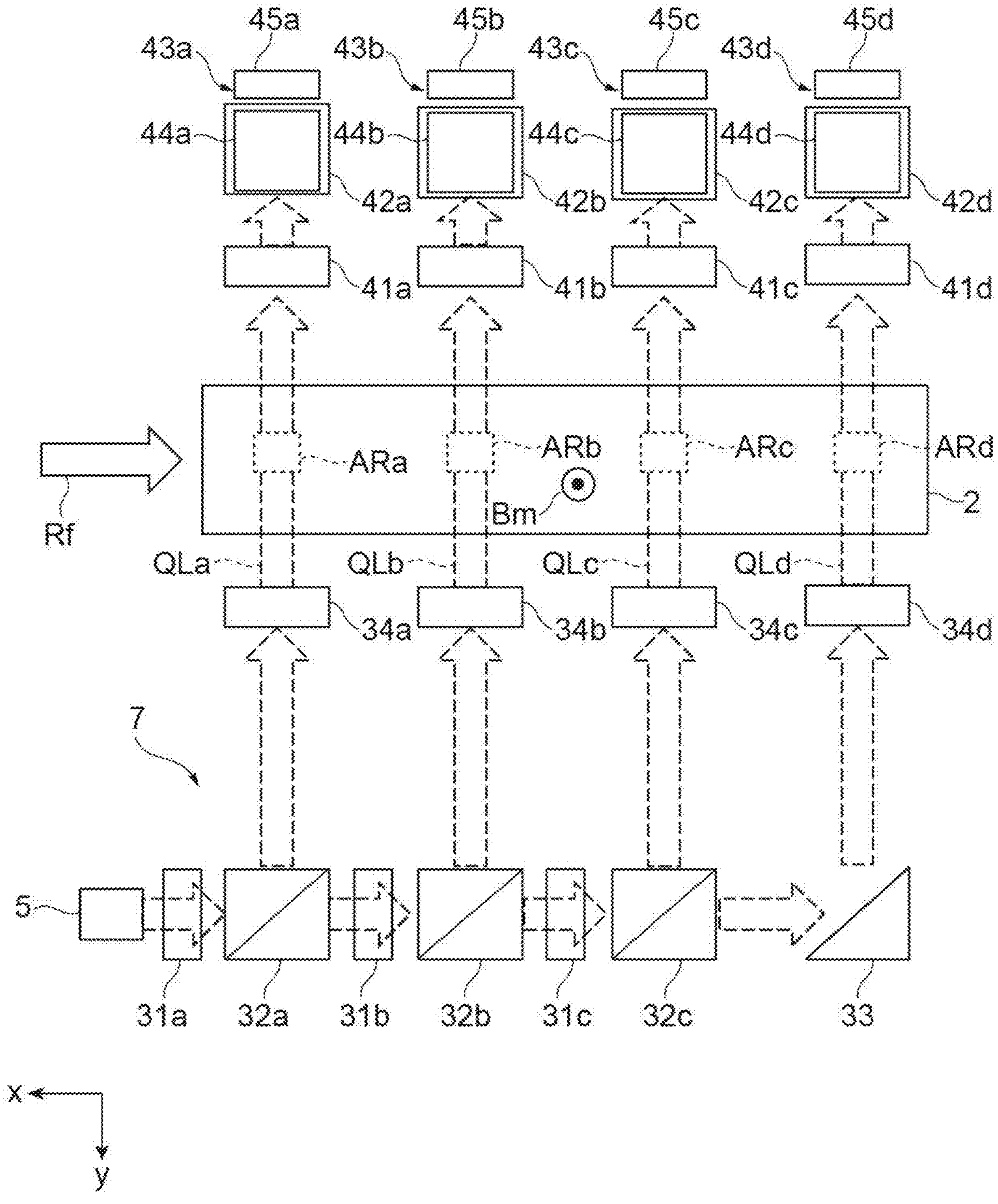
FIG. 4 is a plan view of a second optical system, an optical sensor group, and a third optical system in FIG. 2 as viewed in a −z-axis direction.

Probe light from the probe laser 5 enters the cell 2 via the second optical system 7. FIG. 4 is a plan view of the second optical system 7, the optical sensor group 8, and the third optical system 9 as viewed in the −z-axis direction. The second optical system 7 includes ½ wavelength plates 31*a*, 31*b*, and 31*c*, polarization beam splitters 32*a*, 32*b*, and 32*c*, a total reflection mirror 33, and polarizers 34*a*, 34*b*, 34*c*, and 34*d*.

The ½ wavelength plate 31*a* is provided adjacent to the probe laser 5 in the −x-axis direction, and rotates the polarization plane such that the power of the probe laser is distributed 1:3 by the polarization beam splitter 32*a*. The polarization beam splitters 32*a*, 32*b*, and 32*c* are provided side by side in order in the −x-axis direction with respect to the ½ wavelength plate 31*a*, separate two linearly polarized light components perpendicular to each other from the polarized light component of the probe light transmitted through the ½ wavelength plate 31*a*, transmit one linearly polarized light component in the −x-axis direction, and reflect the other linearly polarized light component in the −y-axis direction. The ½ wavelength plate 31*b* is provided between the polarization beam splitter 32*a* and the polarization beam splitter 32*b*, and rotates the polarization plane of the linearly polarized probe light transmitted through the polarization beam splitter 32*a*. Thus, the probe light can be separated into two linearly polarized light components by the polarization beam splitter 32*b*. The ½ wavelength plate 31*c* is provided between the polarization beam splitter 32*b* and the polarization beam splitter 32*c*, and rotates the polarization plane of the linearly polarized probe light transmitted through the polarization beam splitter 32*b*. Thus, the probe light can be separated into two linearly polarized light components by the polarization beam splitter 32*c*. The total reflection mirror 33 reflects the linearly polarized probe light transmitted through the polarization beam splitter 32*c* in the −y-axis direction.

The polarizers 34*a*, 34*b*, 34*c*, and 34*d* transmit specific linearly polarized light components of the probe light reflected by the polarization beam splitters 32*a*, 32*b*, and 32*c* and the total reflection mirror 33, respectively.

The second optical system 7 having the above configuration is configured such that four systems of probe lights QLa to QLd transmitting through the four polarizers 34*a*, 34*b*, 34*c*, and 34*d* can be incident on the sensitivity regions ARa to ARd intersecting the pump lights PLa to PLd arranged in the longitudinal direction (direction along the x-axis) in the cell 2, respectively.

Referring to FIG. 1, the bias magnetic field coil 11 is a coil that applies a bias magnetic field Bz to the inside of the cell 2 in a direction along the z-axis, and determines the resonance frequency of the electron spin of the alkali metal atom excited inside the cell 2. By the application of the bias magnetic field Bz in the same direction as the incident direction of the pump light by the bias magnetic field coil 11, the axes of the electron spins of the alkali metal atoms excited in the cell 2 are aligned in the direction along the z-axis. When the intensity of the bias magnetic field applied by the bias magnetic field coil 11 is 14 μT and the alkali metal atom is potassium, the resonance frequency of the electron spin is 100 KHz. As described later, the bias magnetic field coil 11 is also shared as a static magnetic field coil used at the time of measuring an MR image by the MRI module.

The bias magnetic field gradient correction coils 12 and 13 are a coil group for correcting a gradient of the bias magnetic field Bz in a direction along the y-axis, a direction along the z-axis, or a direction along the x-axis. The bias magnetic field gradient correction coils 12 and 13 may be configured to include a coil group that corrects gradients in one or two directions of the direction along the y-axis, the direction along the z-axis, and the direction along the x-axis in the bias magnetic field Bz, or may be configured to include a coil group that corrects gradients in three directions. Due to the presence of the bias magnetic field gradient correction coils 12 and 13, even when the bias magnetic field Bz is not uniform due to the influence of an environmental magnetic field or the like, it is possible to perform correction so as to be uniform, and it is possible to enhance the detection sensitivity of the photoexcitation magnetic sensor 1 with respect to the brain magnetic field. As will be described later, the bias magnetic field gradient correction coils 12 and 13 are also shared as the gradient magnetic field coil used at the time of measuring the MR image by the MRI module.

Here, the bias magnetic field gradient correction coils 12 and 13 will be specifically described.

Figure 5:
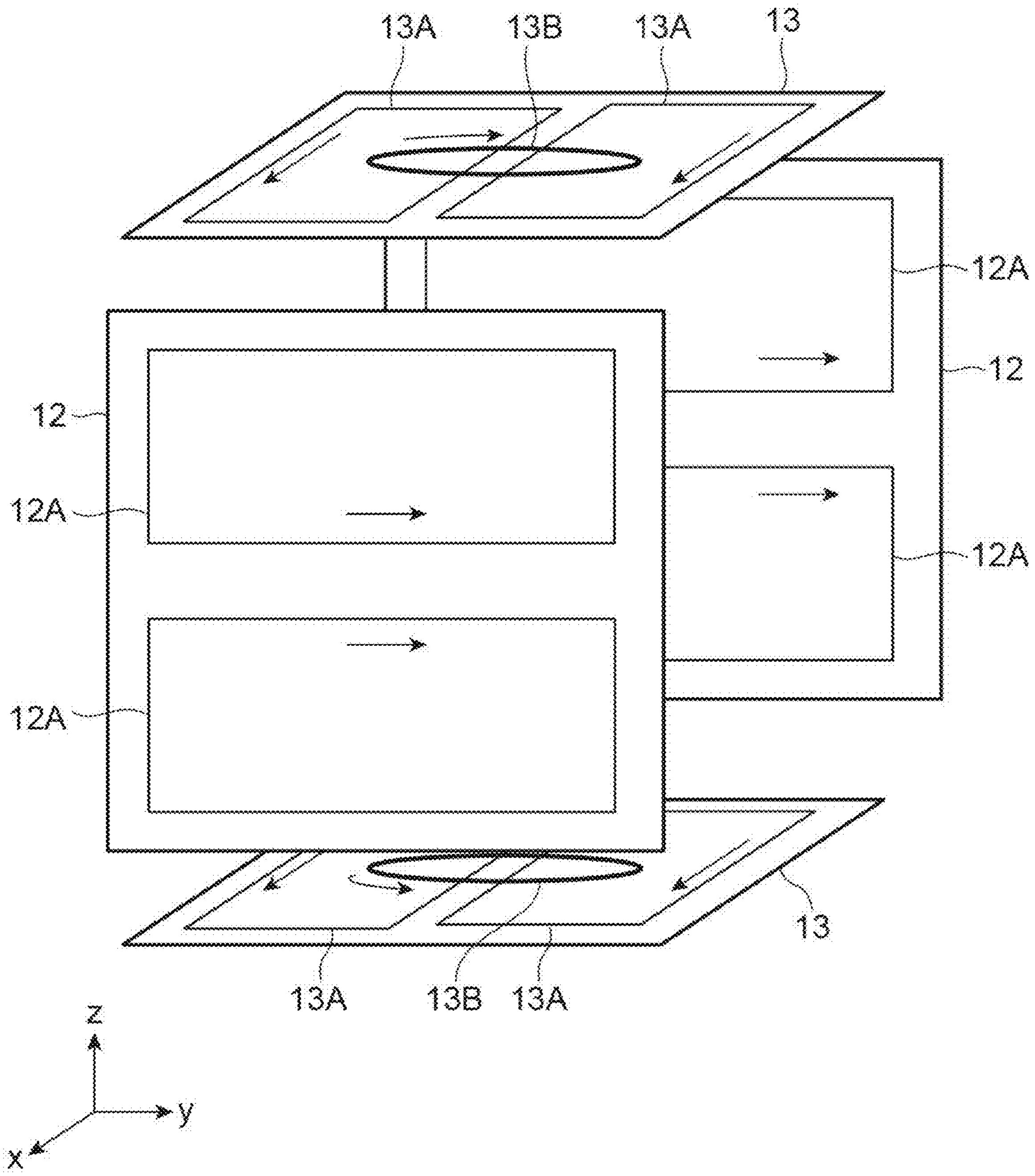
FIG. 5 is a perspective view illustrating a bias magnetic field gradient correction coil of FIG. 1.
Figure 6B:
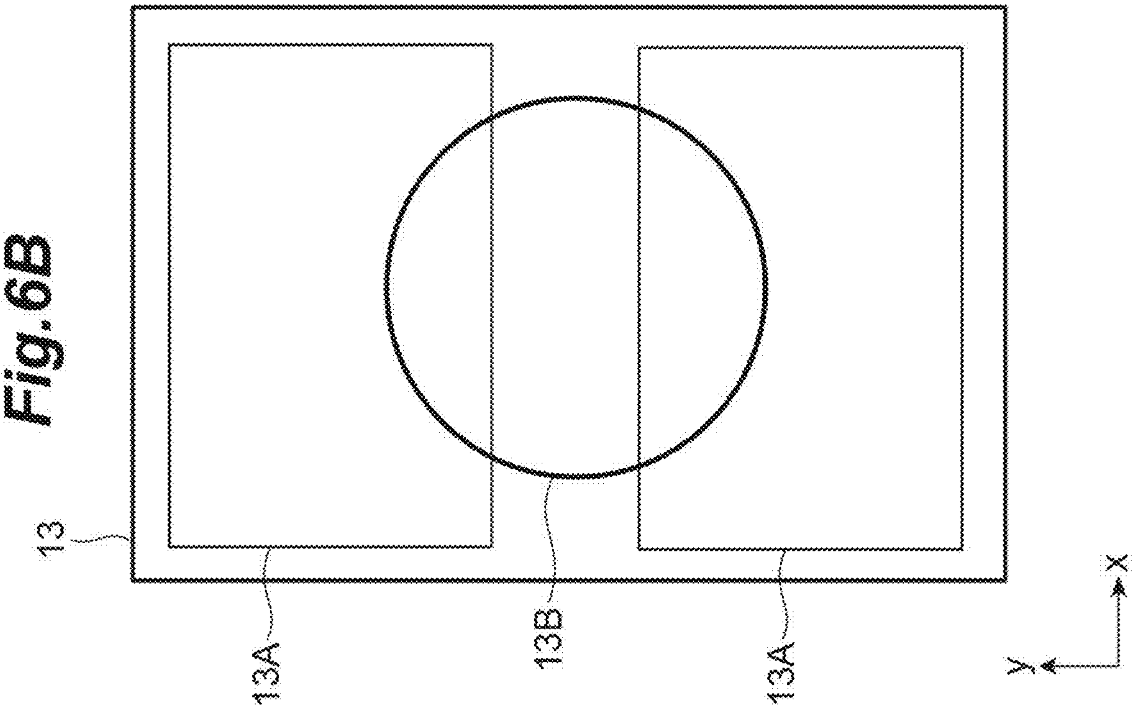
FIG. 6B is a plan view illustrating a first coil and a third coil.
Figure 6A:
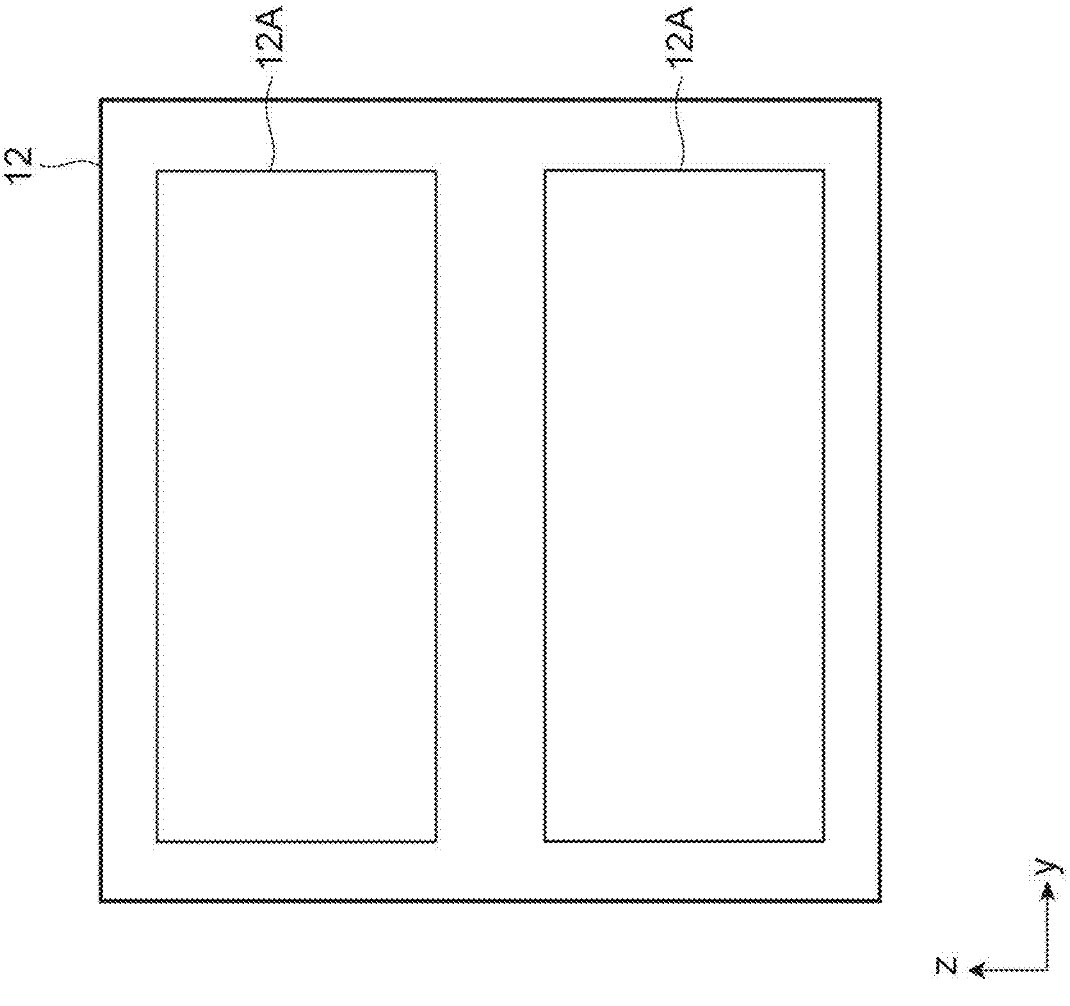
FIG. 6A is a plan view illustrating a second coil.

As illustrated in FIGS. 5 and 6A, the bias magnetic field gradient correction coil 12 is a parallel plate type coil and includes second coils 12A. The second coils 12A are provided on each of a pair of substrates facing each other in the x-axis direction with the cell 2 interposed therebetween. The second coils 12A are disposed on one side and the other side of the cell 2 in the x-axis direction. The second coil 12A corrects the change amount of the bias magnetic field Bz corresponding to the change amount of the position in the x-axis direction. In the illustrated example, the second coil 12A is a parallel four-wire coil.

As illustrated in FIGS. 5 and 6B, the bias magnetic field gradient correction coil 13 is a parallel plate type coil and includes first coils 13A and third coils 13B. The first coils 13A and the third coils 13B are provided on each of a pair of substrates facing each other in the z-axis direction with the cell 2 interposed therebetween. The first coils 13A are disposed on one side and the other side of the cell 2 in the z-axis direction. The first coil 13A corrects the change amount of the bias magnetic field Bz corresponding to the change amount of the position in the z-axis direction. In the illustrated example, the first coil 13A is a parallel four-wire coil. The third coils 13B are disposed on one side and the other side of the cell 2 in the z-axis direction. The third coil 13B corrects the change amount of the bias magnetic field Bz corresponding to the change amount of the position in the y-axis direction. In the illustrated example, the first coil 13A is a Maxell coil.

The first to third coils 13A, 12A, and 13B are coils that correct a first-order gradient magnetic field. Note that the first to third coils 13A, 12A, and 13B may be coils that further correct a second-order gradient magnetic field, and in this case, the uniformity of the bias magnetic field Bz can be further improved. Arrows illustrated in the first to third coils 13A, 12A, and 13B in FIG. 5 indicate directions of applied currents.

The tilting coil 14 (see FIG. 1) generates and irradiates an RF pulse Rf in order to tilt the direction of the electron spin of the alkali metal atom excited in the cell 2 in a direction perpendicular to the incident direction of the pump light. Specifically, the tilting coil 14 generates an RF pulse Rf having the same frequency as the resonance frequency of the electron spin (100 kHz in a case where the intensity of the bias magnetic field Bz is 14 μT and the alkali metal atom is potassium), and irradiates the RF pulse Rf in the −x-axis direction with the intensity and length necessary for the electron spin to tilt by 90 degrees. As tilting devices for tilting the direction of the electron spin instead of the tilting coil 14, means for irradiating another pulsed pump light from a direction orthogonal to the incident direction of the pump light may be provided.

Referring back to FIG. 4, configurations of the optical sensor group 8 and the third optical system 9 will be described.

The third optical system 9 includes ½ wavelength plates 41*a*, 41*b*, 41*c*, and 41*d* and polarization beam splitters 42*a*, 42*b*, 42*c*, and 42*d*. The ½ wavelength plates 41*a*, 41*b*, 41*c*, and 41*d* are provided adjacent to the cell 2 in the −y-axis direction on optical paths of the probe lights QLa, QLb, QLc, and QLd having passed through the sensitivity regions ARa to ARd of the cell 2, respectively, and rotate the polarization planes of the linearly polarized light of the probe lights QLa, QLb, QLc, and QLd having passed through the cell 2. These ½ wavelength plates 41*a*, 41*b*, 41*c*, and 41*d* are rotatably supported about the axis along the y-axis so that the rotation angle of the polarization plane of the probe light can be adjusted. The polarization beam splitters 42*a*, 42*b*, 42*c*, and 42*d* separate two linearly polarized light components perpendicular to each other from the polarized light components of the probe lights QLa, QLb, QLc, and QLd transmitted through the ½ wavelength plates 41*a*, 41*b*, 41*c*, and 41*d*, respectively, transmit one linearly polarized light component in the −y-axis direction, and reflect the other linearly polarized light component in the z-axis direction.

The optical sensor group 8 is an element group that detects polarization plane angles of the probe lights QLa, QLb, QLc, and QLd having passed through the sensitivity regions ARa to ARd, and includes four optical sensor pairs 43*a*, 43*b*, 43*c*, and 43*d*. The optical sensor pair 43*a* includes two photodiodes 44*a* and 45*a*, the photodiode 44*a* outputs a detection signal obtained by detecting the intensity of the other linearly polarized light component of the probe light QLa, and the photodiode 45*a* outputs a detection signal obtained by detecting the intensity of one linearly polarized light component of the probe light QLa. Similarly, the optical sensor pair 43*b*, 43*c*, and 43*d* have two photodiodes 44*b* and 45*b*, two photodiodes 44*c* and 45*c*, and two photodiodes 44*d* and 45*d*, respectively. The two photodiodes 44*b* and 45*b* respectively output detection signals obtained by detecting intensities of two linearly polarized light components of the probe light QLb, the two photodiodes 44*c* and 45*c* respectively output detection signals obtained by detecting intensities of two linearly polarized light components of the probe light QLc, and the two photodiodes 44*d* and 45*d* respectively output detection signals obtained by detecting two linearly polarized light components of the probe light QLd.

Referring again to FIG. 2, the readout circuit 10 is a processing circuit that is electrically connected to the four optical sensor pairs 43*a*, 43*b*, 43*c*, and 43*d* constituting the optical sensor group 8 and processes the detection signals output from the four optical sensor pairs 43*a*, 43*b*, 43*c*, and 43*d*. The readout circuit 10 may be integrated with the control device 109. That is, the readout circuit 10 includes a reading unit that reads the detection signals output from the four optical sensor pairs 43*a*, 43*b*, 43*c*, and 43*d*, and a measurement unit that executes measurement processing of the brain magnetic field in the sensitivity regions ARa to ARd based on the detection signals. The measurement unit may be provided outside the photoexcitation magnetic sensor 1 and configured to execute the measurement processing based on the detection signal output from the photoexcitation magnetic sensor 1.

The readout circuit 10 physically includes a memory such as a RAM and a ROM, a processor (arithmetic circuit) such as a CPU, a communication interface, and an auxiliary storage device such as a hard disk and a semiconductor memory. The readout circuit 10 can be realized by, for example, a personal computer, a cloud server, a smartphone, a tablet terminal, or the like. The function of the readout circuit 10 is realized by executing a program stored in the memory by the CPU of the computer system.

Figure 7A:
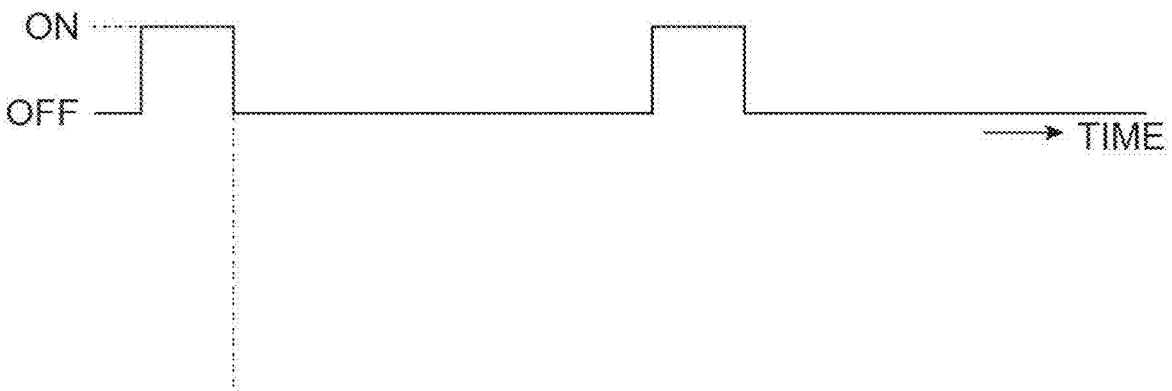
FIGS. 7A to 7C are timing charts illustrating timings of pump light, an RF pulse, and probe light at the time of measurement processing of a brain magnetic field by a readout circuit of FIG. 2.
Figure 7B:
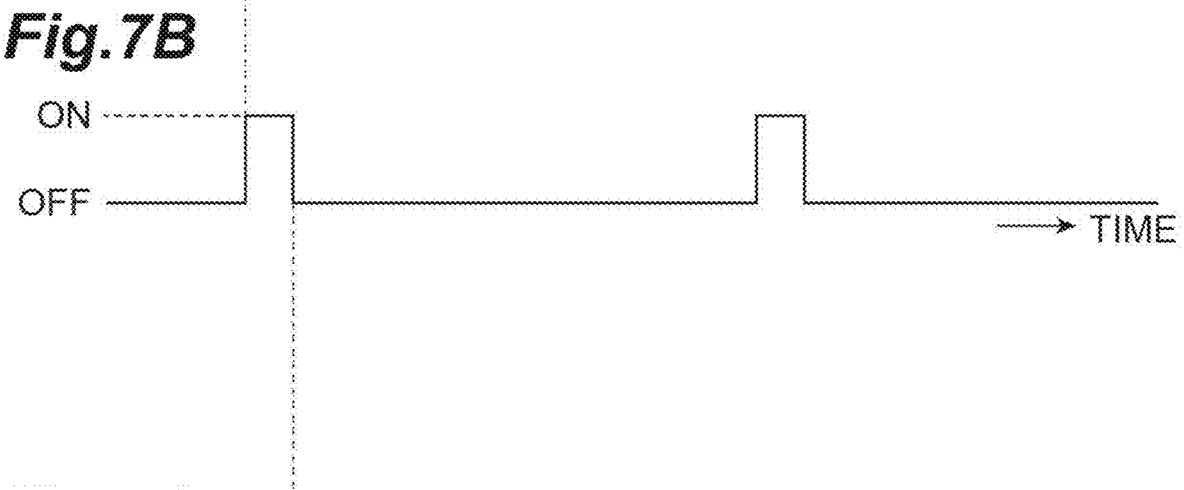
Figure 7C:
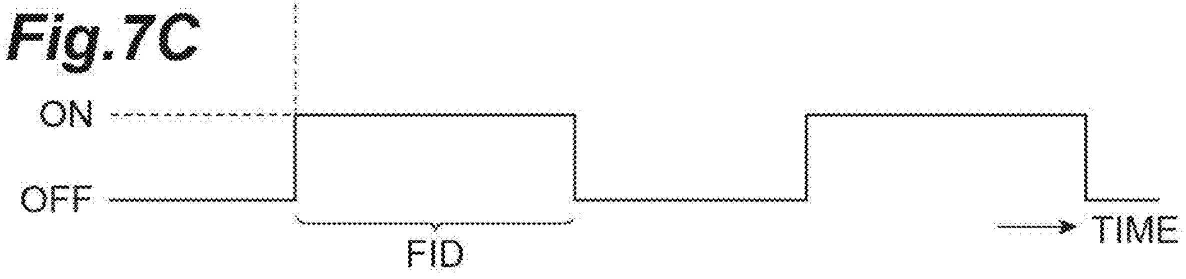
Figure 8:
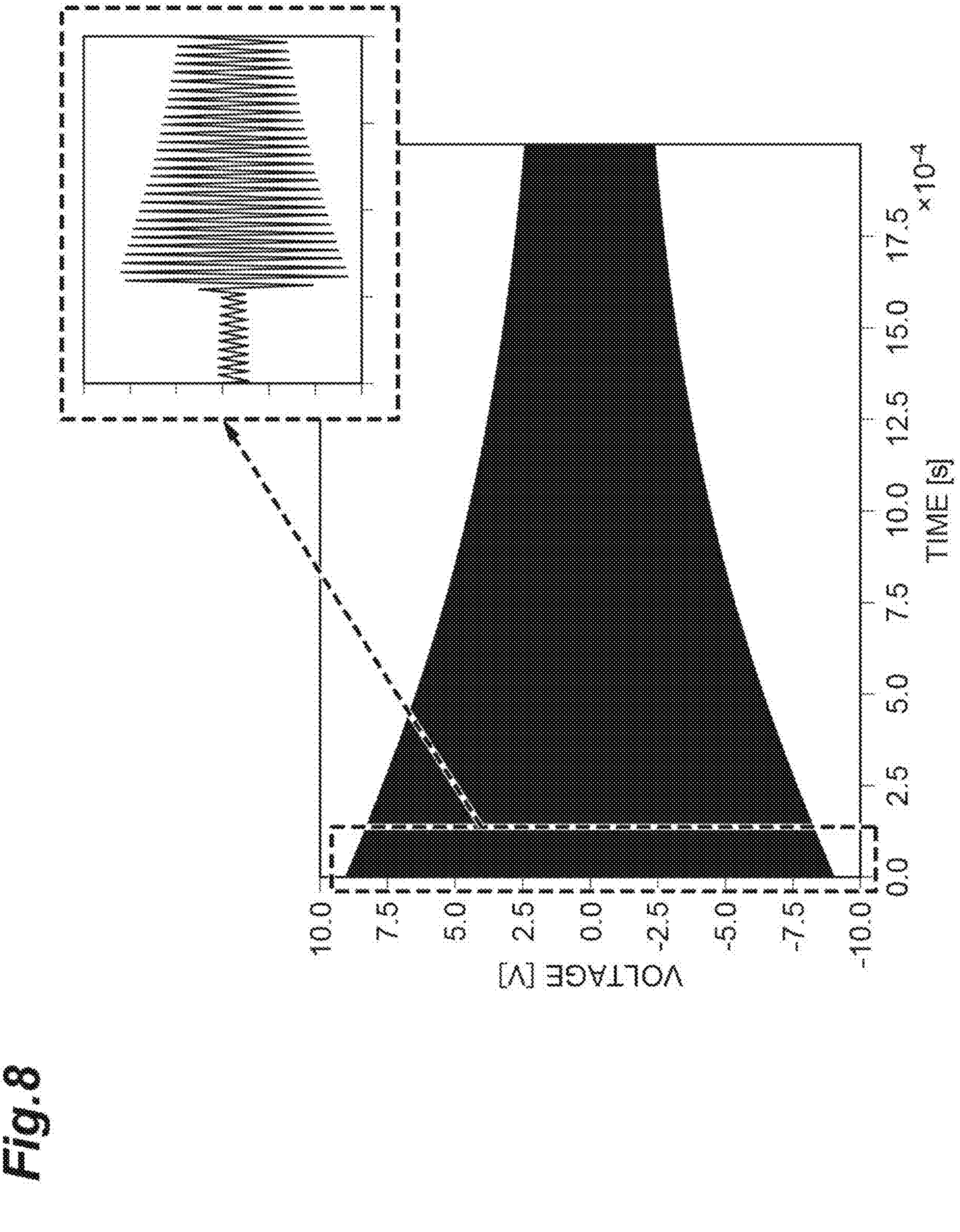
FIG. 8 is a graph illustrating FID acquired by the readout circuit of FIG. 2.

The function of the measurement processing of the brain magnetic field by the measurement unit of the readout circuit 10 will be described with reference to FIGS. 7A to 7C and FIG. 8. FIGS. 7A to 7C illustrate timings of the pump light, the RF pulse, and the probe light at the time of the measurement processing of the brain magnetic field by the readout circuit 10, FIG. 7A illustrates a generation timing of the pump light, FIG. 7B illustrates a generation timing of the RF pulse, and FIG. 7C illustrates a readout timing of the probe light. FIG. 8 is a graph illustrating a temporal change in free induction decay (FID) acquired by the readout circuit 10.

At the time of the measurement processing of the brain magnetic field by the readout circuit 10, control is performed by a control circuit (not illustrated) such that irradiation is performed such that the pump light is repeatedly turned on/off in a pulse shape (FIG. 7A), the RF pulse is irradiated in a pulse shape immediately after the pump light transitions from on to off (FIG. 7B), and the probe light is readout during a predetermined relaxation time after the irradiation of the RF pulse (FIG. 7C). In such a control state, the readout circuit 10 acquires the detection signals output from the four optical sensor pairs 43*a*, 43*b*, 43*c*, and 43*d* during the relaxation time. Then, the readout circuit 10 obtains the FID by taking a difference between the detection signals of the two photodiodes 44*a* and 45*a* constituting the optical sensor pair 43*a* (FIG. 8). Similarly, the readout circuit 10 acquires the FID by taking the difference between the detection signals of two photodiodes also for the optical sensor pairs 43*b*, 43*c*, and 43*d*.

The FID indicates how the electron spin of the alkali metal atom is relaxed, and the frequency of the precession motion of the electron spin changes according to the variation in the brain magnetic field in the sensitivity region ARa, so that the frequency of the vibration changes according to the variation in the brain magnetic field. For example, when the resonance frequency of the electron spin is 100 kHz and the brain magnetic field changes from 0 pT to 1 pT, the frequency of the precession motion changes about 0.007 Hz. By using such a property, the readout circuit 10 derives, with respect to the waveform of the FID at the initial stage of the relaxation time, a frequency $a_1$ of the vibration of the FID, by performing fitting using a function V as shown in the following formula;

$$V = a_0 \sin(2\pi a_1 (t - a_2)) e^{-a_3 t} \quad \text{[Equation 1]}$$

(in the above formula, t indicates a time, and $a_0$, $a_1$, and $a_2$ indicate predetermined parameters), and the frequency $a_1$ is acquired as a measurement value of the brain magnetic field in the sensitivity region ARa. Similarly, the readout circuit 10 acquires measurement values of the brain magnetic field in the sensitivity regions ARb, ARc, and ARd based on the detection signals output from the optical sensor pairs 43*b*, 43*c*, and 43*d*. Furthermore, the readout circuit 10 can acquire time-series data of the measurement values by repeating this operation at a frequency of 100 to 1000 Hz.

Figure 9:
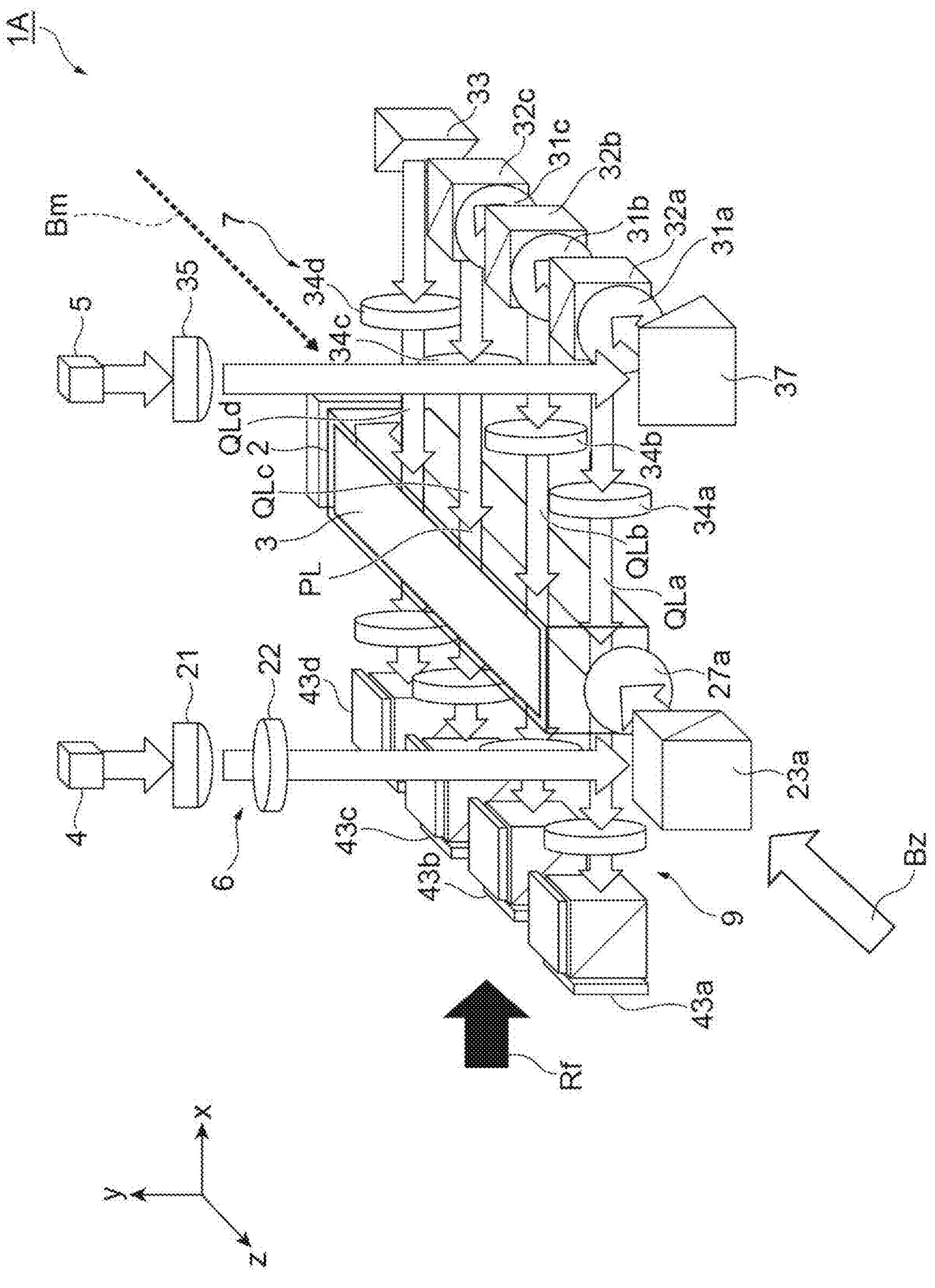
FIG. 9 is a perspective view illustrating a configuration of a photoexcitation magnetic sensor of FIG. 1.

Next, a configuration of the photoexcitation magnetic sensor 1A will be described with reference to FIG. 9. FIG. 9 is a perspective view illustrating a configuration of the photoexcitation magnetic sensor 1A. In the photoexcitation magnetic sensor 1A, the incident direction of the pump light to the cell 2, the application direction of the bias magnetic field Bz to the cell 2, and the irradiation direction of the RF pulse Rf to the cell 2 are different from those of the photoexcitation magnetic sensor 1. Hereinafter, only a configuration different from the photoexcitation magnetic sensor 1 will be described.

The first optical system 6 includes a lens 21, a ½ wavelength plate 22, a polarization beam splitter 23*a*, and a ¼ wavelength plate 27*a*. The polarization beam splitter 23*a* is provided adjacent to the ½ wavelength plate 22 in the −y-axis direction, and reflects the linearly polarized light component in the pump light transmitted through the ½ wavelength plate in the −z-axis direction. The ¼ wavelength plate 27*a* is provided adjacent to the polarization beam splitter 23*a* in the −z-direction, changes the linearly polarized pump light reflected by the polarization beam splitter 23*a* into circularly polarized light, and transmits the pump light in the −z-axis direction. The first optical system 6 having the above configuration is configured such that one system of pump light can be incident in the longitudinal direction (direction along the z-axis) in the cell 2.

The second optical system 7 includes a lens 35, a ½ wavelength plate 36, and a total reflection mirror 37 in addition to the ½ wavelength plates 31*a*, 31*b*, and 31*c*, the polarization beam splitters 32*a*, 32*b*, and 32*c*, the total reflection mirror 33, and the polarizers 34*a*, 34*b*, 34*c*, and 34*d*. The lens 35 is provided adjacent to the probe laser 5 in the −y-axis direction, and condenses the probe light emitted from the probe laser 5 in the −y-axis direction. The total reflection mirror 37 is provided adjacent to the lens 35 in the −y-axis direction, and reflects the probe light transmitted through the lens 35 toward the ½ wavelength plate 31*a* in the −z-axis direction. The second optical system 7 having such a configuration is configured such that each of the four systems of the probe lights QLa to QLd transmitted through the four polarizers 34*a*, 34*b*, 34*c*, and 34*d* can be incident on the four sensitivity regions intersecting the pump light PL arranged in the longitudinal direction (direction along the x-axis) in the cell 2.

Returning back to FIG. 1, the configurations of the MRI module, the power supply device group, and the control device 109 constituting the brain measurement apparatus M1 will be described.

The static magnetic field coil configuring the MRI module is configured by the same coil as the bias magnetic field coil 11 described above. The bias magnetic field coil 11 applies a static magnetic field in the z-axis direction at the time of measuring the MR image. The bias magnetic field coil 11 is switchably connected to either the MRI power supply 106 or the bias magnetic field power supply 107 via the switch 105. At the time of measuring the MR image, the bias magnetic field coil 11 is connected to the MRI power supply 106 under the control of the control device 109, thereby generating a static magnetic field having a predetermined intensity according to the current supplied from the MRI power supply 106. The bias magnetic field coil 11 is connected to the bias magnetic field power supply 107 under the control of the control device 109 at the time of measuring the brain magnetic field, thereby generating a bias magnetic field having a predetermined intensity according to the current supplied from the bias magnetic field power supply 107. As a result, even in a case where the intensity of the bias magnetic field (for example, 14 μT) and the intensity of the static magnetic field (for example, 7 mT) are greatly different, it is possible to stably perform the MR image measurement and the brain magnetic field measurement by sharing the coils having the same number of turns.

The gradient magnetic field coil configuring the MRI module is configured by the same coil as the bias magnetic field gradient correction coils 12 and 13 described above. The bias magnetic field gradient correction coils 12 and 13 apply a gradient magnetic field at the time of measuring the MR image. The bias magnetic field gradient correction coils 12 and 13 generate a gradient magnetic field having a gradient selective to the x-axis direction, the y-axis direction, and the z-axis direction according to the current supplied from the gradient correction power supply 108. The gradient correction power supply 108 supplies a current for gradient correction of the bias magnetic field Bz to the bias magnetic field gradient correction coils 12 and 13 at the time of measuring the brain magnetic field.

The transmission coil 121 is a coil that irradiates (transmits) the head of the subject with an RF pulse (transmission pulse) of a predetermined frequency (for example, about 300 kHz) at the time of measuring the MR image. The transmission coil 121 is disposed, for example, above the head of the subject outside the nonmagnetic frame 104.

The reception amplifier 124 is electrically connected to both ends of the receiver coil 122 via a cable, detects the current output from the receiver coil 122, amplifies the detection result, and outputs the amplified detection result to the control device 109.

The control device 109 controls power supplied to various types of coils at the time of measuring the brain magnetic field and at the time of measuring the MR image, and executes measurement processing of the MR image. The control device 109 is electrically connected to the switch 105, the MRI power supply 106, the bias magnetic field power supply 107, the gradient correction power supply 108, a power supply (not illustrated) for the transmission coil 121, the reception amplifier 124, and the like. The control device 109 physically includes a memory such as a RAM and a ROM, a processor (arithmetic circuit) such as a CPU, a communication interface, and an auxiliary storage device such as a hard disk and a semiconductor memory. The control device 109 can be realized by, for example, a personal computer, a cloud server, a smartphone, a tablet terminal, or the like. The function of the control device 109 is realized by executing a program stored in the memory by the CPU of the computer system.

Specifically, the control device 109 controls switching of the switch 105 between the time of measuring the brain magnetic field and the time of measuring the MR image, connects the bias magnetic field coil 11 and the bias magnetic field power supply 107 at the time of measuring the brain magnetic field, and connects the bias magnetic field coil 11 and the MRI power supply 106 at the time of measuring the MR image. Furthermore, at the time of measuring the MR image, the control device 109 determines currents to be supplied to the bias magnetic field coil 11 and the bias magnetic field gradient correction coils 12 and 13 that operate as coils for applying a static magnetic field and a gradient magnetic field, respectively, and outputs a control signal for outputting the currents to the MRI power supply 106 and the gradient correction power supply 108. That is, the control device 109 determines a current flowing through the bias magnetic field coil 11 so as to apply a magnetic field, as a static magnetic field, in the z-axis direction having a predetermined intensity (for example, 7 mT) to the head of the subject. In addition, the control device 109 selectively determines an x-axis direction magnetic field gradient, a y-axis direction magnetic field gradient, and a z-axis direction magnetic field gradient as the gradient magnetic field, and determines a current flowing through the bias magnetic field gradient correction coils 12 and 13. As a result, it is possible to determine a position to be sliced in the MR image and encode the position in the slice plane by phase encoding and frequency encoding.

In addition, the control device 109 determines the currents to be supplied to the bias magnetic field coil 11 and the bias magnetic field gradient correction coils 12 and 13, and outputs a control signal for outputting the currents to the bias magnetic field power supply 107 and the gradient correction power supply 108 at the time of measuring the brain magnetic field. That is, the control device 109 determines the current flowing through the bias magnetic field coil 11 so as to apply a magnetic field as the bias magnetic field Bz, in the z-axis direction having a predetermined intensity (for example, 14 μT). In addition, the control device 109 determines a current to be supplied to the bias magnetic field gradient correction coils 12 and 13 in order to correct the gradient of the bias magnetic field Bz in the direction along the x-axis, the direction along the y-axis, or the direction along the z-axis.

Furthermore, at the time of measuring the MR image, the control device 109 performs control to irradiate the head of the subject with an RF pulse of a predetermined frequency (for example, about 300 kHz when the intensity of the static magnetic field is 7 mT) by controlling power supplied to the transmission coil 121. As a result, protons of the slice plane (the plane selected by the static magnetic field and the gradient magnetic field) resonate and the spin tilts. Thereafter, the control device 109 controls the power of the transmission coil 121 to be turned off. As a result, the MR image can be acquired by measuring the state in which the spin returns based on the output of the reception amplifier 124. More specifically, the control device 109 measures a nuclear magnetic resonance signal from the protons by encoding a position by a frequency and a phase using a known spin echo sequence, a gradient echo sequence, or the like, and converts the measurement result into an MR image using FFT.

The electromagnetic shield 114 is a shield member that shields high frequency (for example, 10 kHz or more) electromagnetic noise, and is made of, for example, a mesh interwoven with metallic threads, a nonmagnetic metal plate such as aluminum, or the like. The electromagnetic shield 114 is disposed so as to surround the photoexcitation magnetic sensors 1 and 1A, the transmission coil 121, the receiver coil 122, the reception amplifier 124, the nonmagnetic frame 104, the bias magnetic field coil 11, the bias magnetic field gradient correction coils 12 and 13, and the tilting coil 14. The electromagnetic shield 114 can prevent noise in the 300 kHz band, which is a measurement frequency, from entering the receiver coil 122 and increasing at the time of measuring the MR image. In addition, it is possible to prevent the high-frequency noise from entering the photoexcitation magnetic sensors 1 and 1A at the time of measuring the brain magnetic field and the operation from becoming unstable.

Figure 10:
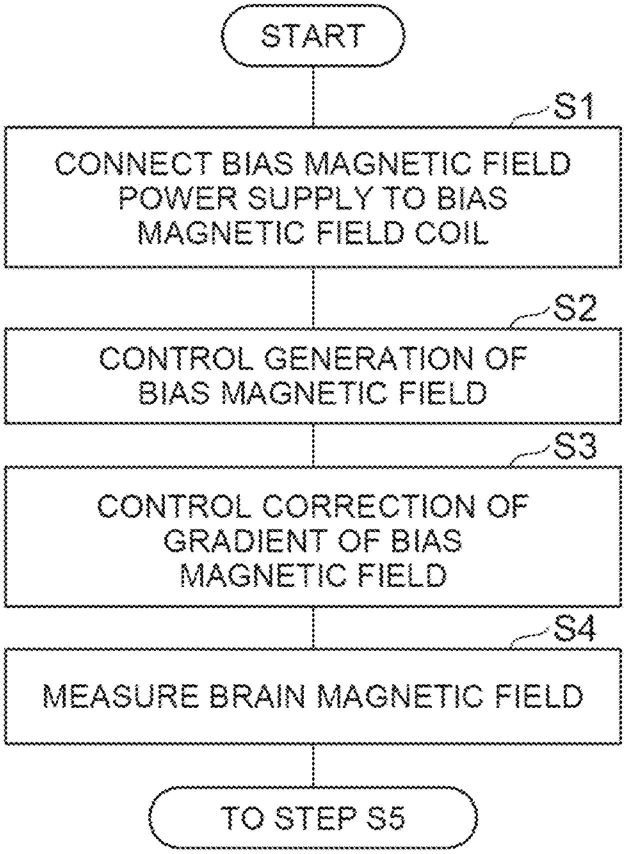
FIG. 10 is a flowchart illustrating an operation of the brain measurement apparatus according to the embodiment.

Next, a brain measurement method using the brain measurement apparatus M1 according to the embodiment will be described with reference to FIGS. 10 and 11. FIGS. 10 and 11 are flowcharts illustrating the operation of the brain measurement apparatus M1.

First, when the measurement of the brain magnetic field is started with the nonmagnetic frame 104 attached to the subject, the control device 109 connects the bias magnetic field coil 11 and the bias magnetic field power supply 107 (step S1). Next, the control device 109 determines a current to be supplied to the bias magnetic field coil 11 for applying a bias magnetic field, and outputs a control signal to the bias magnetic field power supply 107 to control generation of the bias magnetic field by the bias magnetic field coil 11 (step S2). In addition, the control device 109 determines a current to be supplied to the bias magnetic field gradient correction coils 12 and 13 for gradient correction of the bias magnetic field, and outputs a control signal to the gradient correction power supply 108 to control correction of the gradient of the bias magnetic field by the bias magnetic field gradient correction coils 12 and 13 (step S3). In this state, the readout circuit 10 acquires measurement values of the brain magnetic field in a plurality of sensitivity regions of each of the photoexcitation magnetic sensors 1 and 1A in time series (step S4). The readout circuit 10 outputs the acquired time-series measurement values to a predetermined output destination. The predetermined output destination may be an external device such as a terminal device connected via a communication interface in addition to the memory of the readout circuit 10, a storage device such as a hard disk, and an output device such as a display.

Referring to FIG. 11, when the measurement of the MR image is continuously started with the nonmagnetic frame 104 attached to the subject after the measurement of the brain magnetic field is completed, the control device 109 connects the bias magnetic field coil 11 and the MRI power supply 106 (step S5). Then, the control device 109 determines a current to be supplied to the bias magnetic field coil 11 for applying a static magnetic field, and outputs a control signal to the MRI power supply 106 to control generation of the static magnetic field in the z-axis direction in the head of the subject (step S6). Next, the control device 109 determines a current to be supplied to the bias magnetic field gradient correction coils 12 and 13 for generating a gradient magnetic field, and outputs a control signal to the gradient correction power supply 108 to control the generation of a z-axis direction magnetic field gradient (step S7). At the same time, the control device 109 controls the power supplied to the transmission coil 121 so as to irradiate the head of the subject with an RF pulse (step S8). Thus, protons on a predetermined slice plane are excited.

Furthermore, the control device 109 determines a current to be supplied to the bias magnetic field gradient correction coils 12 and 13 for generating the gradient magnetic field, and outputs a control signal to the gradient correction power supply 108, thereby controlling generation of an x-axis direction magnetic field gradient on the slice plane (step S9). As a result, phase encoding is performed. Then, the control device 109 determines a current to be supplied to the bias magnetic field gradient correction coils 12 and 13 for generating the gradient magnetic field, and outputs a control signal to the gradient correction power supply 108 to control generation of a y-axis direction magnetic field gradient on the slice plane (step S10). As a result, frequency encoding is performed.

At the same time, a detection signal of a nuclear magnetic resonance signal from protons is output via the receiver coil 122 and the reception amplifier 124, and accordingly, the control device 109 acquires data of the nuclear magnetic resonance signal (step S11). Thereafter, the control device 109 determines whether to acquire the nuclear magnetic resonance signal data related to another slice plane (step S12). As a result of the determination, when the nuclear magnetic resonance signal data related to another slice plane is acquired ("YES" in step S12), the processing returns to step S7. On the other hand, when the nuclear magnetic resonance signal data related to another slice plane is not acquired ("NO" in step S12), an MR image is acquired by performing Fourier transform on the nuclear magnetic resonance signal data acquired so far (step S13). The control device 109 outputs the acquired MR image to a predetermined output destination. The predetermined output destination may be an external device such as a terminal device connected via a communication interface in addition to a memory of the control device 109, a storage device such as a hard disk, and an output device such as a display.

According to the brain measurement apparatus M1 described above, the electron spin of the alkali metal atom is generated (excited) by emitting the pump light in a state where the bias magnetic field in which the gradient is corrected is applied to the cell 2 in which the alkali metal is filled. Further, the probe light is emitted to a sensitivity region intersecting the pump light in the cell 2, a polarization plane angle of the probe light having passed through the sensitivity region is detected by the optical sensor group 8, and the intensity of the brain magnetic field in the sensitivity region can be measured based on the detected polarization plane angle. In addition, according to the brain measurement apparatus M1, a static magnetic field and a gradient magnetic field are applied by the bias magnetic field coil 11 and the bias magnetic field gradient correction coils 12 and 13, and a nuclear magnetic resonance signal generated by transmission of the RF pulse is detected by the receiver coil 122, whereby a brain morphological image (MR image) can be measured. Here, in the brain measurement apparatus M1, at least one of the static magnetic field coil and the gradient magnetic field coil, which are components of the MRI module, is commonly used as the bias magnetic field coil 11 or the bias magnetic field gradient correction coils 12 and 13, which are components of the magnetoencephalograph module. As a result, the measurement of the brain magnetic field and the acquisition of the brain morphological image (MR image) can be realized by a miniaturized configuration.

In the present embodiment, the static magnetic field coil is configured by the same coil as the bias magnetic field coil 11. As a result, the bias magnetic field and the static magnetic field can be stably applied by the commonly used coil, and stable measurement of the brain magnetic field and the MR image can be realized.

Further, in the present embodiment, the gradient magnetic field coil is preferably configured by the same coil as the bias magnetic field gradient correction coils 12 and 13. As a result, correction of the gradient of the bias magnetic field and application of the gradient magnetic field can be stably performed by the commonly used coil, and stable measurement of the brain magnetic field and the MR image can be realized.

In addition, in the present embodiment, the magnetoencephalograph module is provided with the tilting coil 14 which is the tilting devices for tilting the direction of the electron spin in the direction perpendicular to the pump light. In this case, by measuring the intensity of the brain magnetic field based on the frequency of the change in the polarization plane angle of the detected probe light, the measurement sensitivity of the brain magnetic field can be maintained without being affected by an environmental magnetic field.

Furthermore, in the present embodiment, the tilting coil 14 that irradiates an RF pulse having the same frequency as the resonance frequency is provided as the tilting devices. In this case, the measurement of the brain magnetic field based on the frequency of the change in the polarization plane angle of the probe light can be realized by simple means. Note that the tilting devices may be a light source that irradiates pulsed light. Also in this case, the measurement of the brain magnetic field based on the frequency of the change in the polarization plane angle of the probe light can be realized by simple means.

In addition, the photoexcitation magnetic sensors 1 and 1A according to the present embodiment have sensitivity regions divided into four in a direction along the longitudinal direction of the cell 2. Therefore, the common mode noise can be removed by acquiring the difference value between the measurement values of the brain magnetic field acquired for two adjacent sensitivity regions among the four divided sensitivity regions.

Although various embodiments of the present invention have been described above, the present invention is not limited to the above embodiments, and may be modified or applied to other objects without changing the gist described in each claim.

For example, the photoexcitation magnetic sensors 1 and 1A of the above embodiment have the sensitivity regions ARa to ARd divided into four, but may have any number of sensitivity regions as long as the sensitivity regions are two or more.

In addition, the photoexcitation magnetic sensor 1 of the above embodiment can also adopt a configuration of the following modification.

Figure 12:
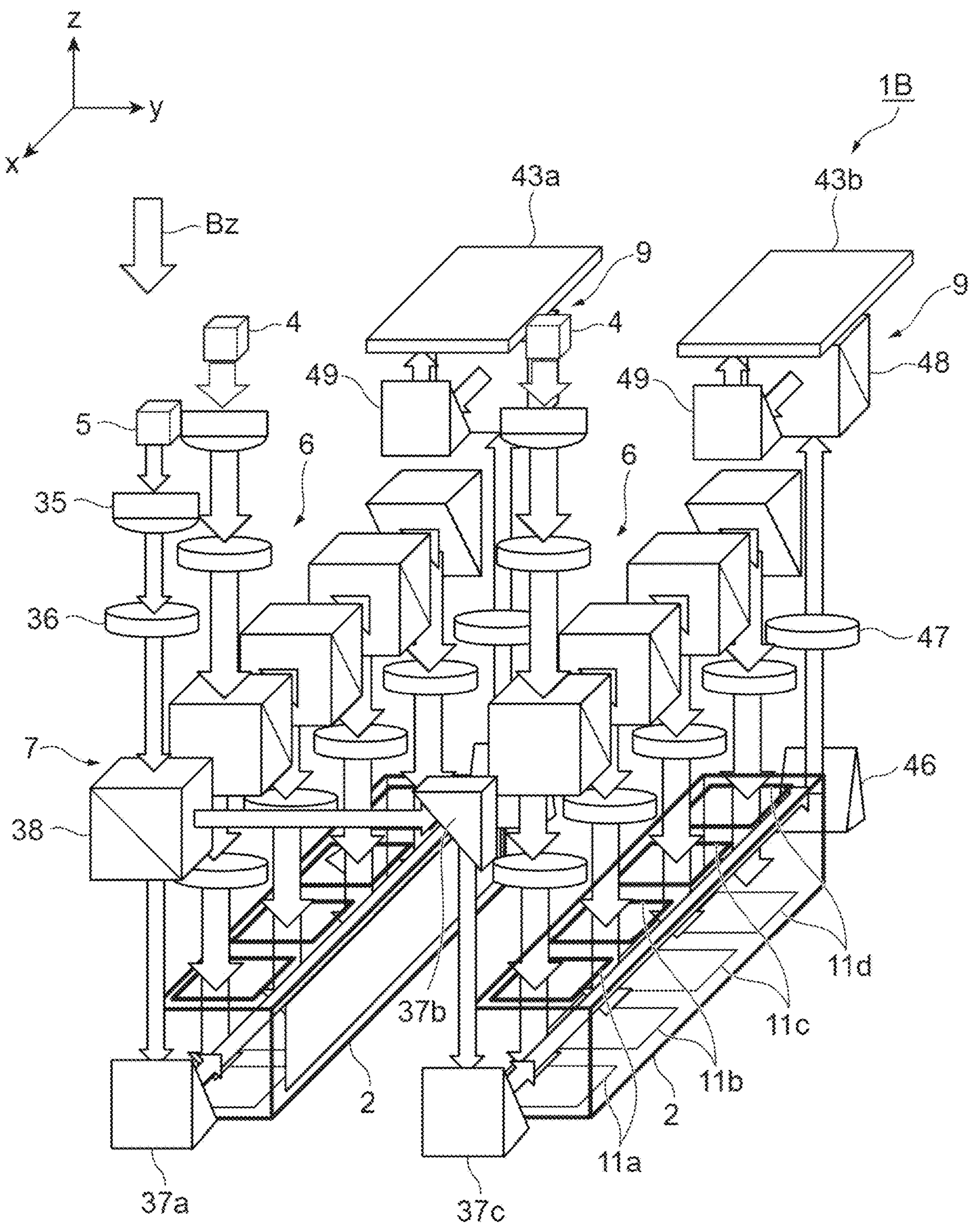
FIG. 12 is a perspective view illustrating a configuration of a photoexcitation magnetic sensor according to a modification.

FIG. 12 is a perspective view illustrating a configuration of a photoexcitation magnetic sensor 1B according to a modification. The photoexcitation magnetic sensor 1B is different from the photoexcitation magnetic sensor 1 in that the photoexcitation magnetic sensor 1B includes two cells 2 arranged in parallel, pump light of four systems is incident on each of the two cells 2, and probe light is branched and incident into the two cells 2 along a longitudinal direction thereof. Hereinafter, only a configuration different from the photoexcitation magnetic sensor 1 will be described.

The photoexcitation magnetic sensor 1B includes a pump laser 4 and a first optical system 6 for causing pump light of four systems to enter regions separated in the longitudinal direction (direction along the x-axis) in the cell 2 corresponding to each of the two cells 2.

In addition, the photoexcitation magnetic sensor 1B includes the second optical system 7 as an optical system for splitting the probe light into two and causing the split probe light to enter the two cells 2. The second optical system 7 includes a lens 35, a ½ wavelength plate 36, a polarization beam splitter 38, and total reflection mirrors 37*a* to 37*c*. The polarization beam splitter 38 is provided adjacent to the ½ wavelength plate 36 in the −z-axis direction, separates two linearly polarized light components perpendicular to each other from the polarized light component of the probe light transmitted through the ½ wavelength plate 36, transmits one linearly polarized light component in the −z-axis direction, and reflects the other linearly polarized light component in the +y-axis direction. The total reflection mirror 37*a* reflects the linearly polarized light component of the probe light transmitted through the polarization beam splitter 38 in the −x-axis direction, and causes the linearly polarized light component to be incident on one of the cells 2 in the longitudinal direction thereof. The total reflection mirrors 37*b* and 37*c* continuously reflect the linearly polarized light component of the probe light reflected by the polarization beam splitter 38 in the −z-axis direction and the −x-axis direction and cause the component to be incident on the other cell 2 in the longitudinal direction thereof. The second optical system 7 having such a configuration is configured such that each of the two systems of probe light can be incident on four sensitivity regions intersecting the pump light arranged in the longitudinal direction (direction along the x-axis) in the cell 2.

In addition, four pairs of bias magnetic field coils 11*a* to 11*d* are provided in each of the two cells 2 included in the photoexcitation magnetic sensor 1B. These bias magnetic field coils 11*a* to 11*d* generate bias magnetic fields having different magnetic field intensities in a stepwise manner in the four sensitivity regions in the cell 2 together with the bias magnetic field coil 11. As a result, the resonance frequencies of the electron spins in the four sensitivity regions in the cell 2 can be set to different values such as 98.5 kHz, 99.5 kHz, 100.5 kHz, and 101.5 kHz.

The photoexcitation magnetic sensor 1B includes two third optical systems 9 and two optical sensor pairs 43*a* and 43*b* corresponding to the two cells 2. The third optical system 9 includes a total reflection mirror 46, a ½ wavelength plate 47, a polarization beam splitter 48, and a total reflection mirror 49. The total reflection mirror 46 reflects the probe light having passed through the cell 2 in the −x-axis direction in the +z-axis direction. The ½ wavelength plate 47 rotates the polarization plane of the probe light reflected by the total reflection mirror 46. The ½ wavelength plate 47 is supported so as to be rotatable about an axis along the z-axis so that the rotation angle of the polarization plane of the probe light can be adjusted. The polarization beam splitter 48 separates the probe light transmitted through the ½ wavelength plate 47 into two linearly polarized light components perpendicular to each other, transmits one linearly polarized light component in the +z-axis direction to be incident on the optical sensor pair 43*a* or the optical sensor pair 43*b*, and reflects the other linearly polarized light component in the +x-direction. The total reflection mirror 49 reflects the other linearly polarized light component reflected by the polarization beam splitter 48 in the +z-axis direction to be incident on the optical sensor pair 43*a* or the optical sensor pair 43*b*.

Also in the photoexcitation magnetic sensor 1B having the above configuration, by including the readout circuit 10, it is possible to execute the measurement processing of the brain magnetic field regarding eight sensitivity regions of 4×2. That is, the readout circuit 10 extracts a specific frequency band corresponding to the resonance frequency of the electron spin in the sensitivity region from the voltage signal generated based on the detection signal of each of the optical sensor pairs 43*a* and 43*b*, and acquires a measurement value of the brain magnetic field based on the voltage signal of the extracted frequency band. The readout circuit 10 can acquire measurement values corresponding to the eight sensitivity regions by repeating extraction of frequency bands and acquisition of measurement values for the eight sensitivity regions.

Also in the above modification, by acquiring the difference between the measurement values regarding the two adjacent sensitivity regions, it is possible to remove the common mode noise and enhance the detection accuracy of the brain magnetic field.

In the above embodiment and the above modification, the linearly polarized pump light is converted into the circularly polarized light, but the circularly polarized pump light may be emitted from the pump laser.

Figure 13:
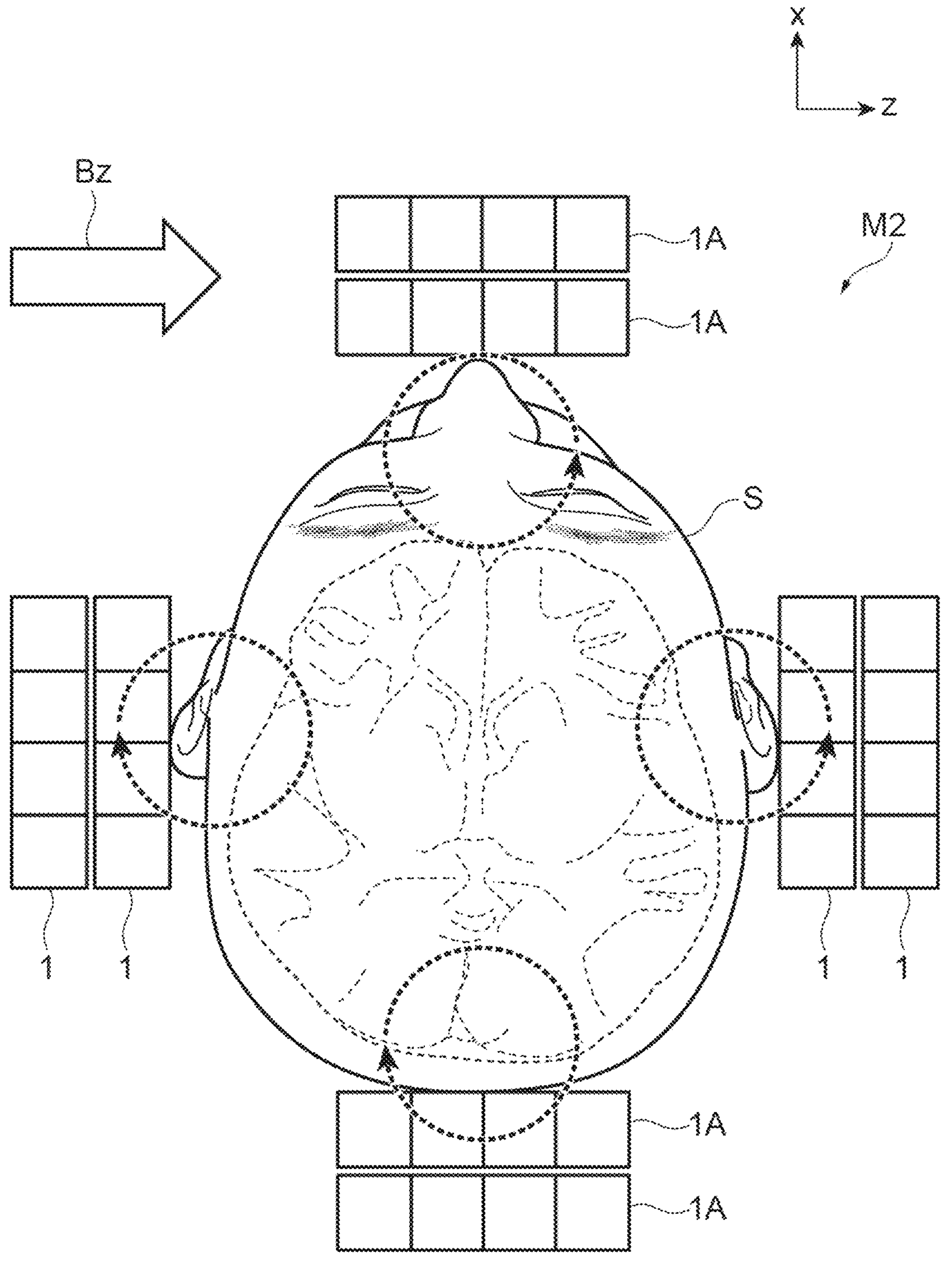
FIG. 13 is a plan view illustrating a configuration of a brain measurement apparatus according to the modification.

In addition, the arrangement of the photoexcitation magnetic sensors 1 and 1A in the brain measurement apparatus M1 can be variously changed. FIG. 13 is a plan view illustrating a configuration of a brain measurement apparatus M2 according to a modification. The brain measurement apparatus M2 includes a plurality of photoexcitation magnetic sensors 1 and a plurality of photoexcitation magnetic sensors 1A provided so as to be arranged around a head (subject) S of the subject. Two photoexcitation magnetic sensors 1A among the plurality of photoexcitation magnetic sensors 1A are arranged in parallel in a predetermined direction (x-axis direction) at positions where the four sensitivity regions are close to and away from the head S. Two photoexcitation magnetic sensors 1 among the plurality of photoexcitation magnetic sensors 1 are also arranged in parallel in a direction (z-axis direction) substantially perpendicular to the arrangement direction of the sensitivity regions in the photoexcitation magnetic sensor 1 at positions where the four sensitivity regions are close to and away from the head S. In addition, the bias magnetic field coil 11, the bias magnetic field gradient correction coils 12 and 13, and the tilting coil 14 are shared between the plurality of photoexcitation magnetic sensors 1 and the plurality of photoexcitation magnetic sensors 1A. The bias magnetic field coil 11 applies a bias magnetic field Bz in the z-axis direction.

According to the brain measurement apparatus M2 having the above configuration, it is possible to acquire a measurement value obtained by measuring a weak magnetic field from the head S.

Specifically, according to the arrangement example of FIG. 13, the measurement value of the magnetic field in the z-axis direction in 8×4=32 sensitivity regions can be acquired. In addition, by acquiring a difference between the measurement value of the sensitivity region close to the head S and the measurement value of the sensitivity region adjacent to the outer side of the head S with respect to the sensitivity region, a weak brain magnetic field from which the common mode noise has been removed can be measured.

Note that, in the brain measurement apparatus M2, a configuration in which the photoexcitation magnetic sensor 1 and the photoexcitation magnetic sensor 1A are arranged only at positions close to the head S and are not arranged in parallel is also applicable. In this case, by acquiring a difference between measurement values of two adjacent sensitivity regions of one of the photoexcitation magnetic sensors 1 and 1A, it is possible to measure the weak magneto-encephalogram from which the common mode noise has been removed.

REFERENCE SIGNS LIST

M1, M2 Brain measurement apparatus
1, 1A, 1B Photoexcitation magnetic sensor
2 Cell
4 Pump laser
5 Probe laser
8 Optical sensor group
11, 11*a* to 11*d* Bias magnetic field coil
12, 13 Bias magnetic field gradient correction coil
121 Transmission coil
122 receiver coil
14 Tilting coil (tilting devices)
ARa to ARd Sensitivity region
Bm Magnetic field
Bz Bias magnetic field
PL, PLa to PLd Pump light
QLa to QLd Probe light
Rf RF pulse
S Head (subject)

What is claimed is:

1. A brain measurement apparatus comprising:
a magnetoencephalograph having:
a cell in which alkali metal vapor is filled,
a pump laser configured to emit pump light for exciting alkali metal atoms constituting the alkali metal vapor,
a probe laser configured to emit probe light for detecting a change in electron spin in an excited state of the alkali metal atoms to a sensitivity region intersecting the pump light in the cell,
an optical sensor configured to detect a polarization plane angle of the probe light having passed through the sensitivity region,
a bias magnetic field coil configured to apply a bias magnetic field in a same direction as a direction of the pump light and determine a resonance frequency of the electron spin, and
a bias magnetic field gradient correction coil configured to correct a gradient of the bias magnetic field; and
an MRI apparatus having:
a static magnetic field coil for applying a static magnetic field,
a gradient magnetic field coil for applying a gradient magnetic field,
a transmission coil for transmitting a transmission pulse of a predetermined frequency, and
a receiver coil configured to detect a nuclear magnetic resonance signal generated by transmission of the transmission pulse, wherein
at least one of the static magnetic field coil and the gradient magnetic field coil is configured by a same coil as the bias magnetic field coil or the bias magnetic field gradient correction coil.

2. The brain measurement apparatus according to claim 1, wherein
the static magnetic field coil is configured by a same coil as the bias magnetic field coil.

3. The brain measurement apparatus according to claim 1, wherein
the gradient magnetic field coil is configured by a same coil as the bias magnetic field gradient correction coil.

4. The brain measurement apparatus according to claim 1, wherein
the magnetoencephalograph further has tilting devices for tilting a direction of the electron spin in a direction perpendicular to the pump light.

5. The brain measurement apparatus according to claim 1, wherein
the magnetoencephalograph has two or more sensitivity regions where the pump light and the probe light intersect with each other, and measures a brain magnetic field based on a difference between outputs of the optical sensors corresponding to two adjacent sensitivity regions.

6. The brain measurement apparatus according to claim 4, wherein the tilting devices irradiates an RF pulse having a same frequency as the resonance frequency.

7. The brain measurement apparatus according to claim 4, wherein the tilting devices irradiates pulsed light.

* * * * *